(12) United States Patent
Montazeri et al.

(10) Patent No.: US 9,804,329 B2
(45) Date of Patent: Oct. 31, 2017

(54) SURFACE PLASMON RESONANT DEVICES AND METHODS OF USE THEREOF

(71) Applicants: Okhtay Montazeri, Hamilton (CA); Nazir Pyarali Kherani, Toronto (CA); Yuan Sheng Fang, Scarborough (CA); Peyman Sarrafi, Toronto (CA)

(72) Inventors: Okhtay Montazeri, Hamilton (CA); Nazir Pyarali Kherani, Toronto (CA); Yuan Sheng Fang, Scarborough (CA); Peyman Sarrafi, Toronto (CA)

(73) Assignee: Okhtay Montazeri, Hamilton, Ontario (CA)

( * ) Notice: Subject to any disclaimer, the term of this patent is extended or adjusted under 35 U.S.C. 154(b) by 265 days.

(21) Appl. No.: 14/292,674

(22) Filed: May 30, 2014

(65) Prior Publication Data

US 2014/0358128 A1 Dec. 4, 2014

Related U.S. Application Data

(60) Provisional application No. 61/829,091, filed on May 30, 2013.

(51) Int. Cl.
| | |
|---|---|
| *G02B 6/34* | (2006.01) |
| *G02B 6/122* | (2006.01) |
| *G02B 6/12* | (2006.01) |
| *A61M 31/00* | (2006.01) |
| *H01L 31/054* | (2014.01) |

(52) U.S. Cl.
CPC ......... *G02B 6/1226* (2013.01); *A61M 31/002* (2013.01); *G02B 6/12002* (2013.01); *G02B 6/12007* (2013.01); *H01L 31/054* (2014.12); *G02B 2006/12095* (2013.01); *G02B 2006/12138* (2013.01); *Y02E 10/52* (2013.01)

(58) Field of Classification Search
CPC ........ G02B 2006/12095; G02B 6/1226; G02B 5/1809; H01L 31/054
See application file for complete search history.

(56) References Cited

U.S. PATENT DOCUMENTS

| | | | |
|---|---|---|---|
| 8,208,191 B2 | 6/2012 | Gan et al. | |
| 8,710,427 B2 * | 4/2014 | Amako | G01N 21/553 250/237 G |
| 8,842,948 B2 * | 9/2014 | Mazumder | G02B 6/1226 385/16 |
| 2004/0155309 A1 * | 8/2004 | Sorin | G01N 21/253 257/433 |

* cited by examiner

*Primary Examiner* — Sung Pak

(57) ABSTRACT

Devices and methods are provided for controlling the propagation of electromagnetic radiation on conductive surfaces via the presence of coupled subwavelength conductor-dielectric unit plasmonic resonators. In some embodiments, the dimensions of the unit plasmonic resonators are selected to produce modal overlap and coupling between surface plasmons of adjacent conductive surfaces. The properties of the unit plasmonic resonators may be spatially graded to produce the slowing down and/or trapping of electromagnetic waves. Methods are provided for calculating resonant modes of structures that involve intra-resonator plasmonic coupling. Various example implementations of such devices and structures are provided.

29 Claims, 14 Drawing Sheets

Top View possible side views

SURFACE PLASMON RESONANT DEVICES AND METHODS OF USE THEREOF

CROSS-REFERENCE TO RELATED APPLICATION

This application claims priority to U.S. Provisional Application No. 61/829,091, titled "SURFACE PLASMON POLARITON RESONANT DEVICES AND METHODS OF USE THEREOF" and filed on May 30, 2013, the entire contents of which is incorporated herein by reference.

BACKGROUND

The present disclosure relates to devices and methods for waveguiding and localizing electromagnetic waves.

When a conductive surface patterned with properly arranged subwavelength features is illuminated by light from a certain range of the electromagnetic spectrum, surface plasmons can be excited. For most metals, this range is in the near-infrared and visible part of the spectrum, where the external field couples to the collective oscillations of the conduction electrons of the metal or a conductor with sufficiently high density of conduction electrons. For simplicity all such conductors with the real part of their permittivity possessing a negative value are simply referred to as conductors herein. At lower frequencies, the near perfect conductivity of the conductor shields the bulk from external radiation. A heuristic approach to circumvent this screening at low frequencies and enhance the penetration of the external fields into the conductor was through the introduction of deep subwavelength corrugations or alternatively by perforating the surface using subwavelength holes into the surface of the conductor. The resulting modes, dubbed spoof surface plasmons, bear resemblance to the visible range plasmonic modes on smooth surfaces where field penetration is significantly more.

It has been shown that such structures are capable of slowing or localizing light when the depth of the corrugations is spatially varied. For example, in U.S. Pat. No. 8,208,191, Gan et al. describe a graded metallic grating structure with a graded depth profile, where the grating consists of grooves having a constant width and a spatially varying depth.

SUMMARY

Devices and methods are provided for controlling the propagation of electromagnetic radiation on conductive surfaces via the presence of coupled subwavelength conductor-dielectric unit plasmonic resonators. In some embodiments, the dimensions of the unit plasmonic resonators are selected to produce modal overlap and coupling between surface plasmons of adjacent conductive surfaces. The properties of the unit plasmonic resonators may be spatially graded to produce the slowing down and/or trapping of electromagnetic waves. Methods are provided for calculating resonant modes of structures that involve intra-resonator plasmonic coupling. Various example implementations of such devices and structures are provided.

Accordingly, in one aspect, there is provided a resonant plasmonic device for guiding and localizing electromagnetic radiation, the resonant plasmonic device comprising:

a support structure comprising a plurality of unit plasmonic resonators;

each unit plasmonic resonator comprising adjacent conductive surfaces having a dielectric region formed therebetween, thereby defining a resonant cavity;

wherein a minimum distance between said adjacent conductive surfaces of at least some of said unit plasmonic resonators is less than approximately 150 nm, such that intra-resonator coupling occurs between surface plasmons excited within said adjacent conductive surfaces; and wherein neighbouring unit plasmonic resonators are configured to support the coupling of electromagnetic energy therebetween; and wherein a spatial gradient in one or more properties of the unit plasmonic resonators exists among at least a subset of said plurality of unit plasmonic resonators.

In another aspect, there is provided a resonant plasmonic device for guiding and localizing electromagnetic radiation, the resonant plasmonic device comprising:

a support structure comprising a plurality of unit plasmonic resonators;

each unit plasmonic resonator comprising adjacent conductive surfaces having a dielectric region formed therebetween, thereby defining a resonant cavity;

wherein neighbouring unit plasmonic resonators are configured to support the coupling of electromagnetic energy therebetween; and wherein a spatial gradient in the effective mode index of the unit plasmonic resonators exists among at least a subset of said plurality of unit plasmonic resonators.

In another aspect, there is provided a method of localizing electromagnetic energy within a resonant plasmonic device, the method comprising:

providing a resonant plasmonic device as described above;

directing propagating electromagnetic radiation onto the resonant plasmonic device such that the propagating electromagnetic radiation couples among adjacent unit plasmonic resonators of said resonant plasmonic device;

wherein the electromagnetic radiation comprises at least one frequency associated with a mode that is localized within one or more unit plasmonic resonators within the resonant plasmonic device;

such that at least a portion of the electromagnetic radiation has a reduced group velocity and is localized within the one or more unit plasmonic resonators.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
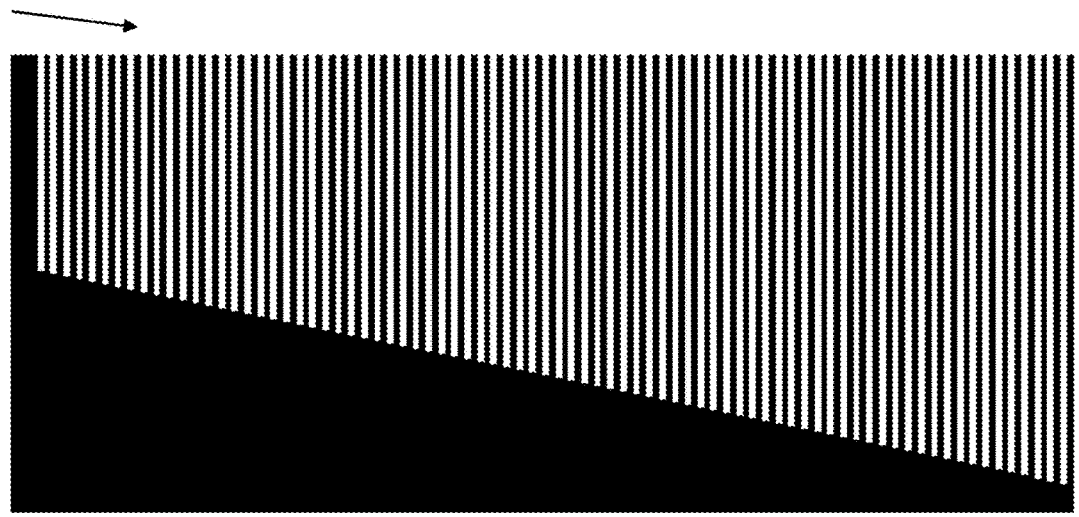
FIG. 1 is an illustration of an example coupled graded resonant plasmonic structure based on a one-dimensional depth gradient.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise stated, the terms "about" and "approximately" mean plus or minus 25 percent or less.

As used herein, the term "dielectric" refers to any polarizable non-conductive medium, including air.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "subwavelength" refers a feature having a characteristic size or dimension that is less than the free-space wavelength of light that is incident on a device or structure.

Coupled Resonant Plasmonic Structures

The present disclosure describes subwavelength plasmonic structures for controlling light propagation and localization among a series of unit plasmonic resonators. In various embodiments, plasmonic structures are described that include a series of subwavelength unit plasmonic resonators that are spatially arranged to support the coupling of electromagnetic waves among neighboring unit resonators, which is henceforth referred to as "inter-resonator coupling".

A "unit plasmonic resonator", as described herein, refers to an externally excitable resonant structure having a dielectric region formed between adjacent conductive surfaces, thereby forming a resonant cavity that is externally excitable via electromagnetic radiation. A unit plasmonic resonator may have a resonant feature that extends in one, two, or three dimensions.

According to various example embodiments described herein, plasmon devices may be provided whereby a support structure includes a plurality of unit plasmon resonators, where the geometry and/or the resonance frequency of the resonator may different among unit plasmonic resonators. Accordingly, several unit plasmonic resonators with differing characteristics may be present, and a coupling may or may not exist between a pair or pairs of the unit resonators.

The coupled nature of the adjacent unit plasmonic resonators of a plasmonic structure results in the spatial transfer of wave energy from one unit plasmonic resonator, near the surface of the resulting extended structure, or, as described below, the transfer of electromagnetic energy between adjacent unit plasmonic resonators may alternatively or additionally occur through the conductive surface or surfaces provided between adjacent unit plasmonic resonators. Such a structure is henceforth referred to as a "coupled resonant plasmonic structure". An example of a unit plasmonic resonator is a groove (also referred to herein as a slit or corrugation) formed within a conductive structure and/or bounded by a conductive surface.

Graded Coupled Resonant Plasmonic Structures

In some embodiments of the present disclosure, graded coupled resonant plasmonic structures are provided such that a spatial gradient is provided in one or more properties of the unit plasmonic resonators among at least a subset of said plurality of electromagnetically-coupled unit plasmonic resonators. For example, in one embodiment, unit plasmonic resonators are provided having a spatial gradient in the width of the unit plasmonic resonators, such that the gradient extends over at least a portion of the unit plasmonic resonators forming the resonant plasmonic structure. For the case of rectangular grooves for example, such width would refer to the spatial separation between the inner conductor-dielectric surfaces of the groove, i.e. the groove walls.

FIG. 1 illustrates a graded coupled resonant plasmonic structure exhibiting a spatial gradient in the depth of corrugations. The figure shows a side view of a conductive structure (i.e. with at least a conductive surface) having a series of planar dielectric corrugations or grooves formed therein, with each corrugation defining a unit plasmonic resonator. Electromagnetic waves incident on the structure, from the direction including that shown by the arrow, couple to at least one resonant mode of coupled resonator plasmonic structure, in which at least a portion of said mode or modes penetrate into the corrugations. As described further below, in some embodiments, the corrugations may be sufficiently narrow to cause intra-resonator coupling between surface plasmon modes excited at adjacent conductive surfaces within at least some of the unit plasmonic resonators forming the resonant plasmonic device.

Figure 2:
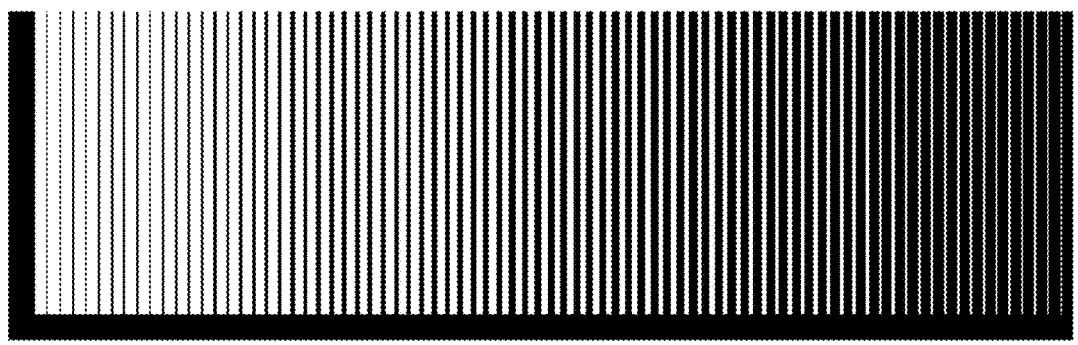
FIG. 2 is an illustration of an example coupled graded resonant plasmonic structure based on a one-dimensional width gradient.

In the embodiment shown in FIG. 2, an alternative embodiment is provided in which a gradient is formed in the dielectric thickness of the unit plasmonic resonators. In the embodiment shown in FIG. 3, the spatial variation in the width of the unit plasmonic resonators is combined with the spatial variation in the depth of grooves.

Figure 3:
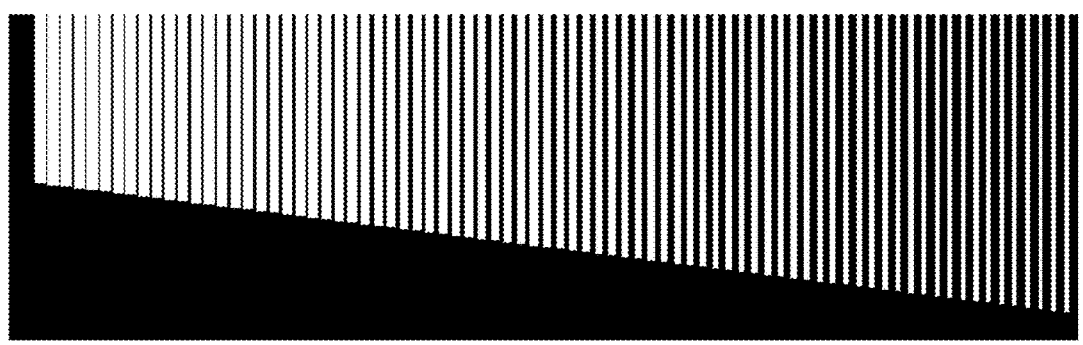
FIG. 3 is an illustration of an example coupled graded resonant plasmonic structure based on a one-dimensional depth and width gradient.

In another example embodiment, a resonant plasmonic structure may be formed having a corrugated structure, similar to that shown in FIGS. 1-3, but where one or more of the grooves have a tapered profile in the longitudinal direction. Such an example embodiment provides a mode index that spatially varies along the longitudinal direction.

It is noted that there is a substantial difference between width-based gratings and depth-based gratings. Depth-based gratings change the resonant cavity modes that the groove (cavity) supports, whereas width-based grooves, through coupling of surface plasmons on the opposing walls of the grooves, change the cavity effective mode index.

This effect of width gradient in controlling the propagation of light can be understood by comparison with gradient index (GRIN) optical fibers of lenses. The presence of a gradient in such an optical structure naturally guides the light in the direction of the increasing index. Thus, light ends up in the highest index medium. Similarly, each groove in plasmonic structure with a width gradient has an effective mode index which increases in the direction of grooves becoming narrower. It will be understood that the coupling in the structures mentioned herein applies to many mode types such as even and odd modes with cut-off and those without cut-off. When the modes do not have cut-off, the grooves can become as narrow as possible, continuing to increase the effective mode index and squeeze and localize shorter and shorter wavelengths. At the same time, structures involving a smooth and gradual decrease of the mode index acts as an impedance-matching mechanism and allows energy to flow from one groove to a neighboring slightly narrower groove.

In yet another embodiment (not shown), a gradient may be provided in the pitch or spacing of the unit plasmonic resonators, optionally while maintaining a constant thickness within each unit plasmonic resonator.

A gradient in one or more properties of the unit plasmonic resonators may be employed to slow or stop light propagation within a graded coupled resonant plasmonic structure. In one example implementation, electromagnetic energy may be localized in a resonant plasmonic device by directing propagating electromagnetic radiation onto the resonant plasmonic device such that the propagating electromagnetic radiation couples among adjacent unit plasmonic resonators (for example, directing electromagnetic radiation such that it is incident onto one side of the device and serially couples among adjacent unit plasmonic resonators), where the electromagnetic radiation includes at least one frequency associated with a mode that is localized within one or more unit plasmonic resonators of the device. The portion of the electromagnetic radiation having the frequency associated with the localized mode will propagate with a reduced group velocity as it approaches the location associated with the localized mode, such that it is slowed and localized at the position of the localized mode.

For example, through a slow variation of the thickness in a spatial direction (generally the direction of wave propagation within the structure) the resonance frequency of each unit plasmonic resonator slowly changes in the spatial direction. Furthermore, the effective mode index within each groove may be increased by decreasing the width of the unit plasmonic resonator. It is known that light slows down in the vicinity of resonances. Since the resonances of the unit plasmonic resonators are spatially spread out, a light wave comprised of more than one frequency component (such as white light in the visible part of the spectrum) will slow down in different spatial regions of such a structure.

In other embodiments of the present disclosure, graded coupled plasmonic structures are provided having a spatial variation in the dielectric constant of the dielectric within the unit plasmonic resonators, as further described below.

Multiply-Coupled Resonant Plasmonic Structures

In some embodiments, the unit plasmonic resonators may be configured to support intra-resonator plasmonic coupling between multiple surface plasmons such that the dispersion relation of a coupled resonant plasmonic structure is modified. For example, when the adjacent conductive surfaces forming a unit plasmonic resonator are placed within close proximity of each other, the surface plasmon modes associated with the adjacent surfaces can become coupled through the coupling provided by the overlap of the evanescent fields of the surface plasmon modes between two or more conductor-insulator interfaces of the unit plasmonic resonator. Accordingly, the electromagnetic waves interacting with such structures involve the formation of coupled surface plasmons, as opposed to merely "spoof surface plasmons", as previously described by others, which refers to the enhanced field penetration into the surface of the conductor through perforating or grating of the surface. Furthermore, without intending to be limited by theory, it is expected that such coupled surface plasmons within a unit plasmonic resonator may be excited beyond the electromagnetic frequencies normally associated with plasmon generation, for example, farther into the infrared. Henceforth any medium with a negative-valued real part of the permittivity below a prescribed frequency is referred to as a conductive medium. For metals, this condition is satisfied below the bulk plasmon frequency.

Accordingly, in some embodiments, a unit plasmonic resonator having two or more adjacent conductive surfaces may be configured such that the adjacent conductive surfaces are sufficiently close to facilitate coupling between surface plasmons associated with each conductive surface forming the unit plasmonic resonator. Accordingly, a unit plasmonic resonator may have at least one dimension that is sufficiently small to result in strong intra-resonator coupling between adjacent conductive surfaces.

It will be understood that the phrase "adjacent conductive surfaces" may refer to several different geometric configurations of the conductive surfaces. In one example, planar surface segments may be spatially separated by a dielectric, such as in the case of a resonant plasmonic structure having a linear (e.g. one dimensional) array of unit plasmonic resonators (e.g. a corrugated resonant device) where the unit plasmonic resonators are formed between adjacent planar conductive surfaces. In another example, a unit plasmonic resonator may be formed having a longitudinal extend and closed cross-section, such as a longitudinally extended dielectric segment that having a conductive lateral surface (and one or more open ends or apertures to facilitate coupling between adjacent resonators and/or to externally propagating electromagnetic energy). For example, the unit plasmonic resonator may have a square or rectangular cross section (or a cross-section having another polygonal shape characterized by opposing sides), where intra-resonator coupling occurs between one or more pairs of opposing sides (depending on the manner in which the unit plasmonic resonators are spatially arranged, and/or depending on the direction and/or polarization of the incident electromagnetic energy). It will be understood that the geometry of a unit plasmonic resonator having a closed cross-section need not be polygonal, but could be any oblong shape (such as an ellipse) that can characterized by opposing surface segments.

Figure 17:
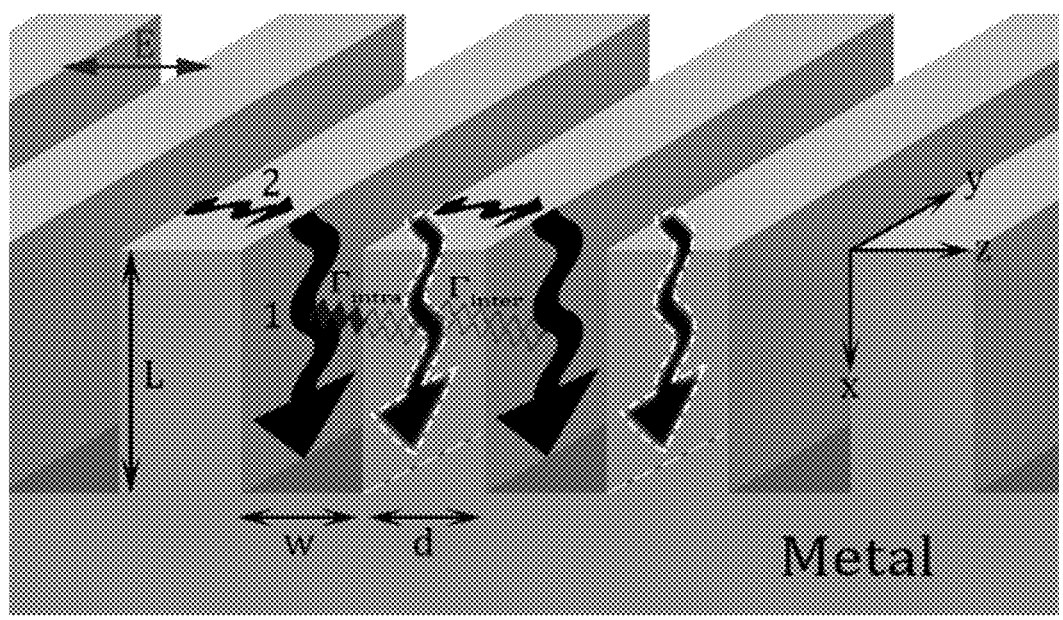
FIG. 17 is an illustration showing the various example mechanisms of inter-resonator coupling.

It will be understood that coupled surface plasmons may be excited on pairs of opposing walls (provided that the separation is sufficiently small to support strong coupling, as noted above), when the pair of plasmons support the excitation of a p-polarized SP mode in the cavity. For example, referring to FIG. 17, if the groove (infinite in the y direction) is turned into square cross-section dielectric region in the conductor (e.g. extending all the way through the thickness of the conductor) in x direction, but limited in the y and z directions by a thickness t, then this new system will support surface plasmonic excitations based on two pairs of orthogonally polarized light, one for each pair of walls. Similarly, surface plasmon pairs may be excited between adjacent surfaces for hexagons, and octagons, and other polygonal structures in the same manner.

In yet another example, the coupling between surface plasmons of the unit plasmonic resonator can be mediated externally through the conductor or a dielectric even when the cross-section of the cavity are polygons with an odd number of sides. One example embodiment is shown in FIG. 18, for the simplest case of triangular cross section, though it is understood that it is applicable to other cross sections with an odd number of sides.

In yet another example, a particular polarization of light can be coupled to the opposite walls of a groove, when the cross-section of the groove is a polygon with an even number of sides, and the separation between the said opposite walls are sufficiently small to support intra-resonator plasmonic coupling. In yet another example, a unit plasmonic resonator having a cylindrical cross section may also effectively exhibit intra-resonator coupling if the diameter of the cylinder is sufficiently small.

In general, a unit plasmon resonator may be formed when a pair of adjacent metal-dielectric interfaces are provided, having dielectric therebetween.

Figure 18:
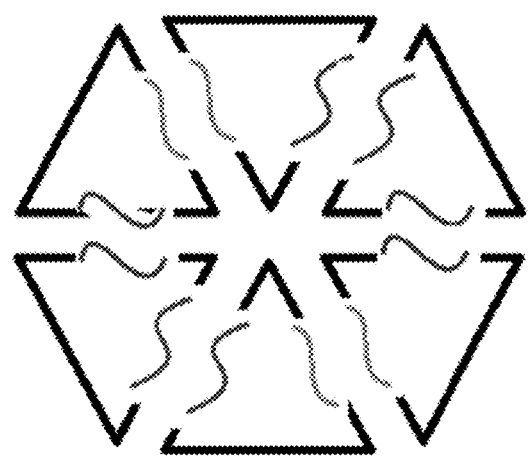
FIG. 18 is an illustration of an example plasmonic resonant device in which unit plasmonic resonators are formed between conductive structures having a closed cross-section.

FIG. 18 illustrates the different forms of intra- and inter-resonator coupling that may be achieved within a resonant plasmonic device. The inter-resonator coupling between the unit plasmonic resonators can be through either a dielectric or a conductor. As shown in the figure, P-polarized radiation (E-field in the z-direction) can launch surface plasmons travelling in the x-direction in the xy plane into the grooves (labeled 1), as well as surface plasmons travelling in the z-direction. In narrow grooves, two type-1 surface plasmons couple and form the intra-groove coupling $\Gamma_{intra}$, when $\omega$ becomes smaller than approximately 150 nm. Likewise, two resonant cavities couple when d is comparable in size to the skin depth of surface plasmons in the metal, which acts to reinforce intergroove coupling, shown as $\Gamma_{inter}$.

A secondary mechanism of intergroove coupling is through surface plasmons travelling in the z-direction in the yz plane (labeled 2). Such coupling mechanism utilizes a conductive surface on the top of the device in order to support the additional surface plasmons. However, it will be understood that such a top conductive surface is not a requirement of the device, as other coupling mechanisms may be employed.

It will be understood that the insulator provided between adjacent conductive interfaces need not be formed from a single material, or from a homogeneous material. For example, in one example embodiment, a unit plasmonic resonator may be formed from two different adjacent metal-insulator interfaces, optionally with different metals and different insulators, such as, for example, an silver-$SiO_2$ interface joined with an air-gold interface.

In some embodiments, a resonant plasmonic structure may include unit plasmonic resonators formed from adjacent conductive surfaces having dielectric therebetween, where the adjacent conductive surfaces are surfaces of different conductive structures, and where each conductive structure has a closed cross-section. For example, a resonant plasmonic structure may be provided having unit plasmonic resonators formed between adjacent surfaces of conductive structures having a triangular cross section, as shown in FIG. 18.

The unit plasmonic resonators can be modeled as providing coupling between three surface plasmons. In polygonal cross sections with odd number of sides, there will be 3 surface plasmons on each metal-insulator surface, and in an arrangement that that allows another parallel surface of a neighbor's nearby, the same phenomena occur. See, for example, FIG. 18, where the black triangular sides are conductors and the spacing in between them is a dielectric or a conductor through which a plasmonic coupling can take place.

This coupling of surface plasmons both within the subwavelength resonators (intra-resonator coupling) and among adjacent resonators (inter-resonator coupling; leading to the confinement of light over the structure), is herein referred to as "multiple coupling", and "multiple confinement".

Intra-resonator coupling generally occurs when the minimum width of the dielectric gap within a unit plasmonic resonator is sufficiently small to cause strong modal overlap of the electric field associated with the surface plasmons. Such strong modal overlap has been found to occur, over a broad range of wavelengths of incident electromagnetic radiation, when the minimum distance between adjacent conductive surfaces is less than approximately 150 nm. Accordingly, in some illustrative example implementations, a unit plasmonic resonator may have a minimum conductive surface separation that is less than approximately 150 nm, less than approximately 100 nm, less than approximately 50 nm, or less than approximately 25 nm.

Accordingly, as used herein, the phrases "multiple coupling", "multiple confinement" may refer to the coupling of surface plasmons both within the subwavelength resonators and to the electromagnetic coupling of adjacent resonators within a coupled resonant plasmonic structure. A coupled resonant plasmonic structure having unit plasmonic resonators configured for multiple coupling is henceforth referred to as a "multiply-coupled resonant plasmonic structure". In some embodiments, the inter-resonator coupling, or the coupling of adjacent resonators is weak in comparison to the intra-resonator plasmonic coupling. In yet another embodiment, the inter-resonator coupling is strong, referred to in some literature as the strong coupling regime.

Graded Multiply-Coupled Resonant Plasmonic Structures

The ability to tailor the intra-resonator plasmonic coupling of surface plasmons within a unit plasmonic resonator enables additional degrees of freedom in the design and properties of subwavelength devices and systems. In some embodiments of the present disclosure, a multiply-coupled resonant plasmonic structure may exhibit a spatial variation in the intra-resonator plasmonic coupling between surface plasmons. This variation in the coupling of surface plasmons may be achieved, for example, by varying one or more properties of the unit plasmonic resonators. In another embodiment, this variation in the coupling of surface plasmons may be achieved, for example, by varying the strength of inter-resonator coupling. In yet another embodiment, this variation in the coupling of surface plasmons may be achieved, for example, by varying the strength of intra-resonator coupling. This spatial variation in the plasmonic coupling may be employed to produce multiply coupled resonant plasmonic structures where at least one mode is spatially localized. Such structures are henceforth referred to as "graded multiply-coupled resonant plasmonic structures."

It is noted that the mere spatial variation in the depth of a corrugation, while maintaining a constant spacing between adjacent conductive surfaces, does not produce an appreciable spatial variation in the coupling between surface plasmons within the unit plasmonic resonators. Accordingly, such structures are not graded multiply-coupled plasmonic structures.

In particular, the depth grating disclosed in U.S. Pat. No. 8,208,191, by Can et al. is neither a multiply-coupled resonant plasmonic structure, nor a graded multiply-coupled resonant plasmonic structure. The structure of Gan et al. is not multiply-coupled because the spacing between adjacent conductive surfaces within each grating corrugation is too wide to support substantial intra-resonator plasmonic coupling between adjacent surface plasmons. In other words, the width of the corrugations in the grating structure of Gan et al. is too large to produce strongly confined overlap between the surface plasmons on the adjacent conductive surfaces. This lack of strong confinement and strong coupling and lack of modal overlap fails to produce an appreciable effect on the dispersion relation of the structure. For example, the large width of the corrugations in the structures provided by Can et al. prevents the localization of different modes based on a width-based gradient, and only provides for multiple mode localization based on a height gradient, as can be seen from FIG. 7A.

In some embodiments of the present disclosure, graded multiply-coupled resonant plasmonic structures are provided having a spatial variation in at least the width of the unit plasmonic resonators. The variation in the width of the unit plasmonic resonators, such that neighbouring unit plasmonic resonators have different thicknesses of dielectric between their respective adjacent conductive surfaces, results in a spatial variation in the intra-resonator plasmonic coupling of the surface plasmons. The spatial variation in the width of the unit plasmonic resonators may be combined with the spatial variation in one or more additional properties of the unit plasmonic resonators, such as a variation in the depth of grooves or corrugations.

A gradient in the dielectric thickness of the unit plasmonic resonators may be employed to guide, slow, or stop light propagation within a graded multiply-coupled resonant plasmonic structure. Through a slow variation of the thickness in a spatial direction (generally the direction of wave propagation within the structure) the resonance frequency of each unit plasmonic resonator slowly changes in the spatial direction. It is known that light slows down in the vicinity of resonances. Since the resonances of the unit plasmonic resonators are spatially spread out, a light wave comprised of more than one frequency component (such as white light in the visible part of the spectrum) will slow down in different spatial regions of such a structure.

In some embodiments of the present disclosure, graded multiply-coupled plasmonic structures are provided having a spatial variation in the dielectric constant, or a spatial variation in the effective mode index within the unit plasmonic resonators. Such a variation in the dielectric constant or the effective mode index, such that neighbouring unit plasmonic resonators have different dielectric constants or different mode indices, results in a spatial variation in the coupling of dual surface plasmons within the unit plasmonic resonators.

Methods of Calculating Resonances of Multiply-Coupled Resonant Plasmonic Structures In some embodiments, the dispersion relation (and/or other properties of parameters) of a multiply-coupled resonant plasmonic structure may be calculated by including, into a mathematical model, an interaction between the surface plasmon modes that may be present on adjacent conductive surfaces within a unit plasmonic resonator. The present section provides one example method for performing such a calculation, where the coupling between adjacent surface plasmons within each unit plasmonic resonator is modeled to predict the dependence of resonant modes on one or more parameters of the overall multiply-coupled resonant plasmonic structure (such as gradients in one or more dimensions).

In conventional modelling of plasmonic structures, one is usually interested in waves propagating in the plane of multi-layered plasmonic waveguides. However, in embodiments disclosed herein, such as the semi-infinite unit plasmonic resonators shown in FIGS. 1-3 in which a dielectric is bound by a metal surface on one end, the unit plasmonic resonators are placed at right angles to the propagation direction of the electromagnetic wave. In yet another embodiment, the said dielectric can be unbounded on both ends, so that the top surface of coupled resonant plasmonic structure is connected via the dielectric with the bottom surface of the coupled resonant plasmonic structure, where the said top and bottom surfaces correspond to the two ends of the unit plasmonic resonators. Accordingly, the unit plasmonic resonators are end-fire coupled to the propagating wave.

Provided herein is an example model accounting for propagation and plasmonic excitation in such a configuration, where an analytical surface plasmonic theory is employed to describe each individual unit plasmonic resonator. The present example model explains the behaviour of composite structures of such unit plasmonic resonators, even when intra-resonator plasmonic coupling and multiple gradients in height and thickness are introduced. The inventors have found that the present example model explains existing phenomena in gratings, and may also be employed to design and/or predict the performance of new structures. Effects such as light propagation control, slow-light and light trapping applications may be analyzed according to the present example model, and variations thereof.

Figure 4:
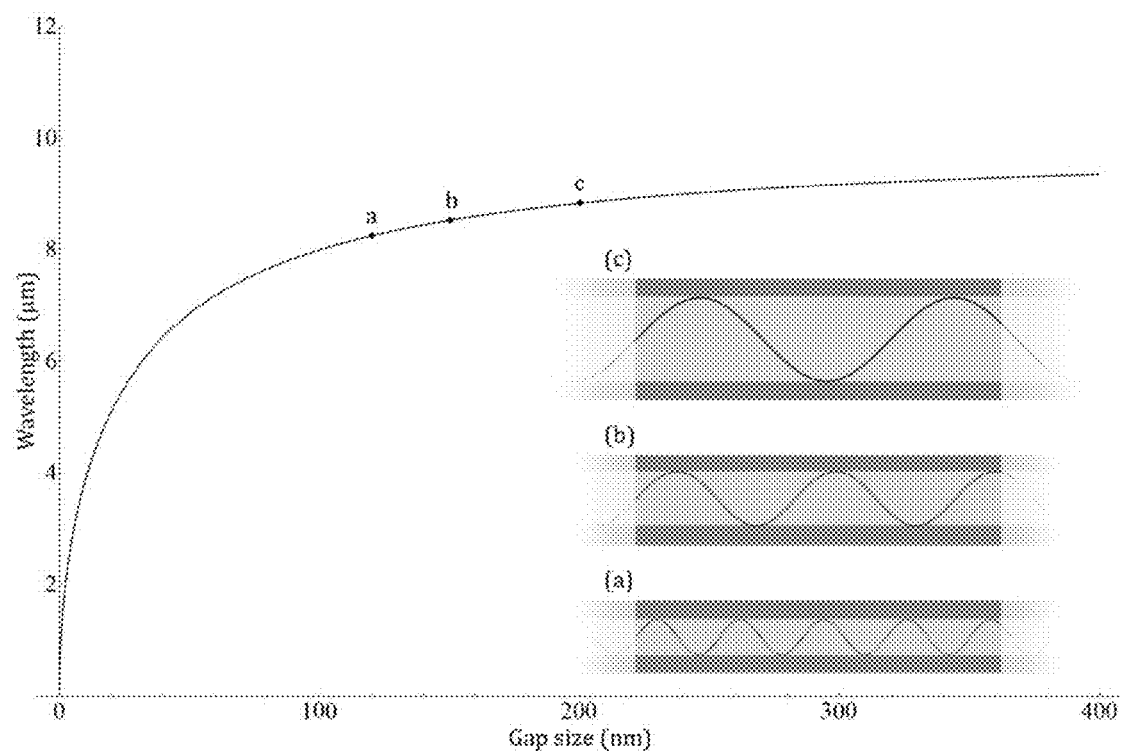
FIG. 4 plots the dependence of the surface plasmon wavelength on gap size. The inset illustrates the effect of the gap size on the wavelength of the plasmonic modes excited within a unit plasmonic resonator, where, as the gap thickness increases, and less coupling occurs among adjacent surface plasmons, the resonant wavelength approaches the conventional cavity resonance of the resonator.

According to the present example model, a plasmonic waveguide, as shown in FIG. 4, may be modeled as follows. The non-oscillatory TM bound modes in the direction normal to the interface in the core region are coupled, where $-t/2 < z < t/2$, which yields:

$$H_y = C e^{i\beta x} e^{k_1 z} + D e^{i\beta x} e^{-k_1 z}, \qquad (1)$$

$$E_x = -iC \frac{1}{\omega \varepsilon_0 \varepsilon_1} k e^{i\beta x} e^{k_1 z} + iD \frac{1}{\omega \varepsilon_0 \varepsilon_1} k e^{i\beta x} e^{-k_1 z},$$

$$E_z = C \frac{\beta}{\omega \varepsilon_0 \varepsilon_1} e^{i\beta x} e^{k_1 z} + D \frac{\beta}{\omega \varepsilon_0 \varepsilon_1} e^{i\beta x} e^{-k_1 z}.$$

where $k_1 \equiv k_{z1}$ for shorthand, $k_1 = \sqrt{\beta^2 - \varepsilon_2 k_0^2}$ is the component of the wave vector perpendicular to the interfaces, $$k_0 = \frac{\omega}{c},$$

$\omega$ is the frequency of excitation, $\varepsilon_0$ is the permittivity of free space, and $\varepsilon_1$ is the permittivity of the core, usually a dielectric, and $\varepsilon_2$ is the permittivity of the cladding sandwiching the core, usually a metal, though this could be interchanged in some embodiments. This expression results from adding the two solutions in the core region of thickness t and applying continuity conditions.

The dispersion relation of the waveguide may then be derived based on the expressions shown in equation 1. For the odd modes which have no cutoff within an MIM waveguide one obtains:

$$\tanh\left(k_1 \frac{w}{2}\right) = -\frac{k_1 \varepsilon_1}{k_2 \varepsilon_2}. \qquad (2)$$

where $k_2 = \sqrt{\beta^2 - \varepsilon_2 k_0^2}$.

FIG. 4 shows the calculated surface plasmon wavelength $\lambda_{sp} = 2\pi/\text{Re}(\beta)$, as calculated from Eq. (2) as a function of the core thickness t. For large thicknesses, $\lambda_{sp}$ approaches the limiting case of the classical cavity resonator whose resonant frequency is simply determined by the length of the structure. An example of a classical cavity resonator is an open-pipe wind instrument such as a flute, where the resonant pitch only depends on the length of the flute.

FIG. 4 clearly illustrates, however, that unlike classical cavity resonators, the structure thickness also changes the resonant frequency of the unit plasmonic resonator. This becomes most prominent as the thickness falls below approximately 100 nm, where the slope of the curve increases quickly.

Using Eq. (2), the $n_{\text{eff}}$ or the effective mode index of the cavity is found to be $$n_{\text{eff}} = \sqrt{\frac{\alpha^2 \varepsilon_1 \varepsilon_2^2 - \varepsilon_1^2 \varepsilon_2}{\alpha^2 \varepsilon_2^2 - \varepsilon_1^2}}, \qquad (2.5)$$

where $$\alpha \equiv \tanh\left(\frac{k_1 t}{2}\right)$$

for shorthand.

Figure 5:
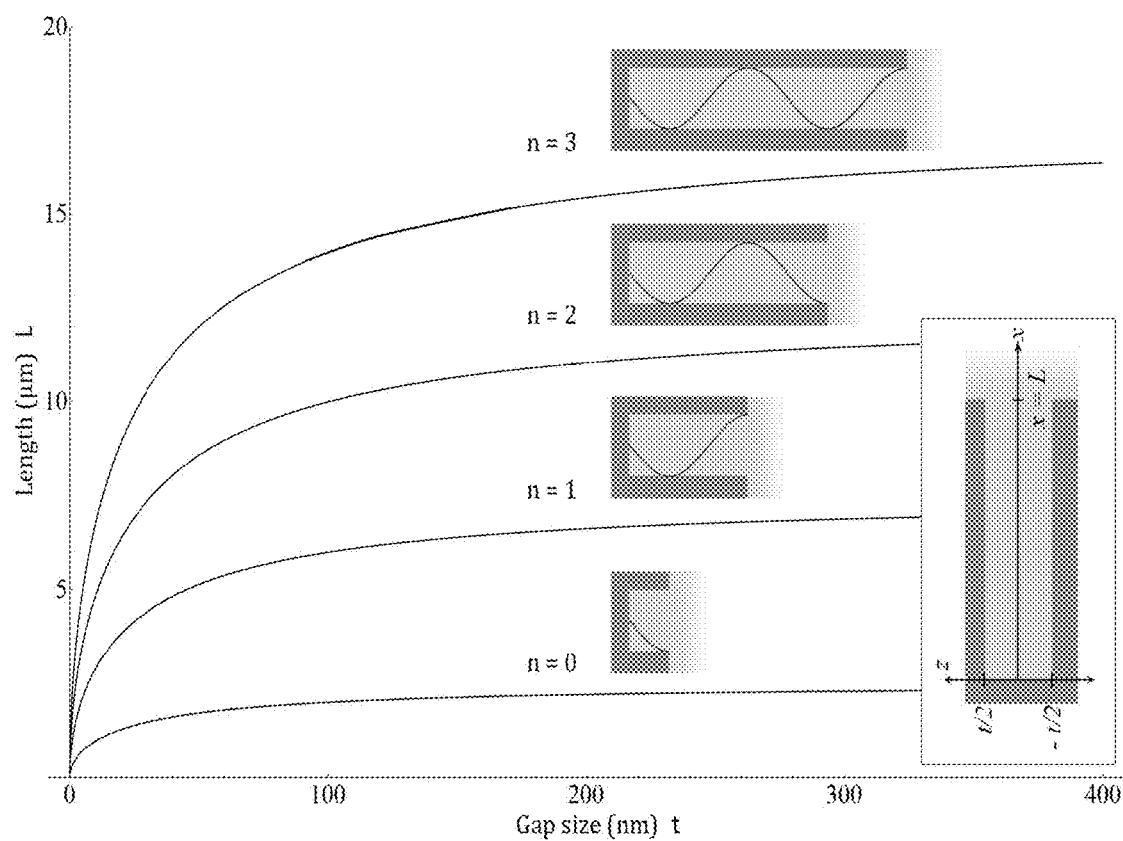
FIG. 5 shows the structure and response of a unit plasmonic resonator having one closed end, where graph shows the dependence of the first four modes on gap size and gap length, and where the inset illustrates the length L and thickness t.

In one example implementation, the model may be extended to address the multiply coupled resonant plasmonic structures described above. As shown in FIG. 5, each unit plasmonic resonator in such a structure is modeled as a waveguide that is terminated on one end by the same metal as the cladding, and on the other end by the same insulator as the core. In order to accurately incorporate the aforementioned plasmonic effects into such terminated unit plasmonic resonators, the following continuity conditions are applied:

$$E_{z1}|_{x=0} + E_{z2}|_{x=0} = 0, \qquad (3)$$

due to the perfect electric conductor at the bottom of the resonator, and $$\frac{\partial (H_{y1} + H_{y2})}{\partial x}\bigg|_{x=L} = 0 \quad (4)$$

due to the near unity reflection from near the top of the resonator, where $\beta >> \sqrt{\varepsilon} k_o$.

Combining conditions (3) and (4) with a model of a plasmonic waveguide such as a metal-dielectric-metal waveguide, the resonant behavior of a multiply-coupled resonant plasmonic structure is found to be described by:

$$\left(\frac{1}{4} + \frac{n}{2}\right)\lambda_{sp} = L. \quad (5)$$

where n is the order of the mode.

FIG. 5 shows the fundamental and three higher modes of a single unit plasmonic resonator. The ordinate represents the length of the resonator L and the abscissa refers to the thickness t.

In yet another implementation, the plasmonic waveguide resonator can be bounded on both ends in such a way that the cladding terminates however the core remains continuous such as when through or via holes or slots are made into the conductive structure. In such cases, a similar argument to that presented above holds, except that the cavity modes will have two maxima at both ends, such as the case of open cylinder air column whose fundamental resonant modes start at $\lambda/2$.

It is seen that the plasmonic effects are most notably observed for small thicknesses and for higher order modes. When t or the thickness of the core is very small, the coupling of plasmonic modes represented by Eq. (1) becomes quite pronounced. Accordingly, if an initial unit plasmonic resonator in the shape of a groove with a closed end is squeezed or compressed width-wise such that the intra-resonator thickness t decreases, the trapped modes are blue-shifted so that the resonant modes of the unit plasmonic resonator are shifted to a higher frequency mode or modes. Conversely, as the thickness of the groove is increased, the plot of the n=0 mode quickly approaches a horizontal asymptote, which is the familiar classical waveguide cavity oscillator response (such as the case of air columns or wind instruments) that is insensitive to the thickness.

It can be seen that for higher order modes, the curves do not flatten out as quickly as the fundamental mode, and the present coupled plasmonic calculation gives a much more accurate account of their behavior. It can further be seen that in the limiting case of $t \to 0$ all unit plasmonic resonator modes converge and we get the limiting case of bulk metal as expected. This is further evident from Eq. (2.5) that when $t \to 0$ (that is, in the metal-insulator-metal case, bringing the conductive walls closer and shrinking the dielectric gap,) $n_{eff} \to \sqrt{\varepsilon_2}$ and the effective index of the metal is recovered.

It is noted that normally field penetration into flat metal surfaces is on the order of skin-depth which prevents electromagnetic waves from profoundly penetrating a medium of such index. However, through introduction of deep sub-wavelength grooves, holes, or slots, and with the assistance of the surface plasmons reinforcing each other through intra-groove plasmon coupling and giving rise to a mode with no cutoff, the external fields are able to reach deep into the metal. Such a metal surface becomes particularly important into the infrared wavelengths, where field penetration in the metals is nearly nonexistent and metals behave as near perfect conductors. This phenomenon is also fundamentally related to spoof SPPs where perforations or corrugations spoof surface plasmons with overall effects that are similar to real SPPs as shown by Pendry, et al.

At the other extreme, where $t \to \infty$ (separating one wall from the other, resulting in a single vertical wall)

$$n_{eff} = \sqrt{\frac{\varepsilon_1 \varepsilon_2}{\varepsilon_1 + \varepsilon_2}}$$

which is that of a flat metal-insulator interface. Engineering a grating with a tapered $n_{eff}$ through the very gradual tapering of w, results in a metasurface with a spatially varying effective index that modifies the fundamental and higher resonant modes of the plasmonic groove. Eq. (2.5) shows that engineering the impedance of structured metal surfaces through subwavelength grooves defines an effective medium with the range of $$n_{eff} \in \left(\sqrt{\frac{\varepsilon_1 \varepsilon_2}{\varepsilon_1 + \varepsilon_2}}, \sqrt{\varepsilon_2}\right).$$

Examples of Calculated Mode Profiles

Figure 6A:
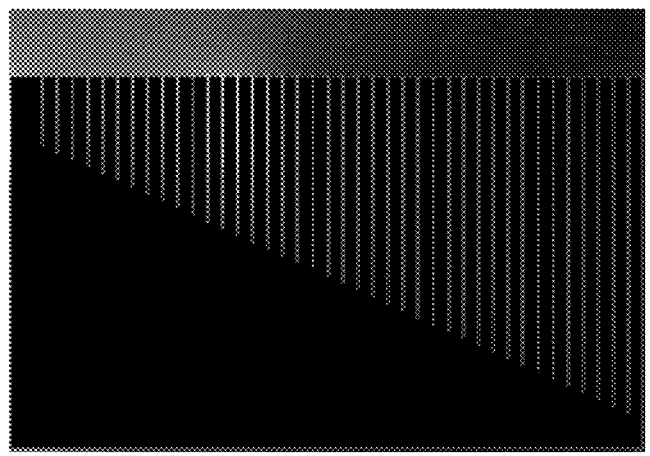
FIGS. 6A-C show (A) an illustration the location of light trapping in a tapered grating structure of groove width 15 nm; (B) the same geometric gradient as in (A) but with a gap size of 35 nm, showing a shift in the location entrapment; and (C) a family of curves showing the first four modes of the coupled plasmonic resonator; points A and B on the lowermost curve identify the fundamental modes corresponding to the gratings.
Figure 6B:
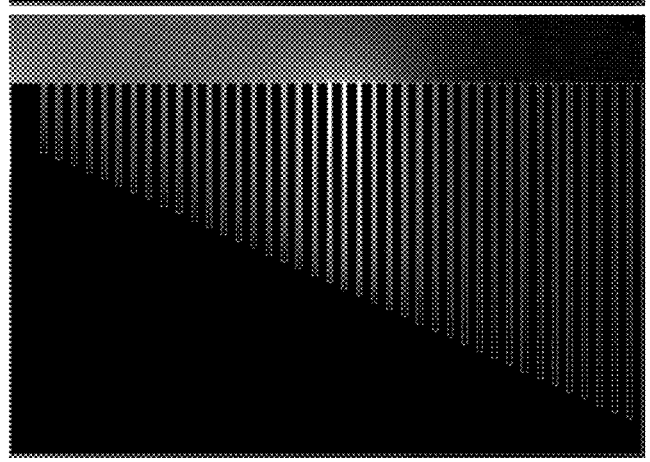
Figure 6C:
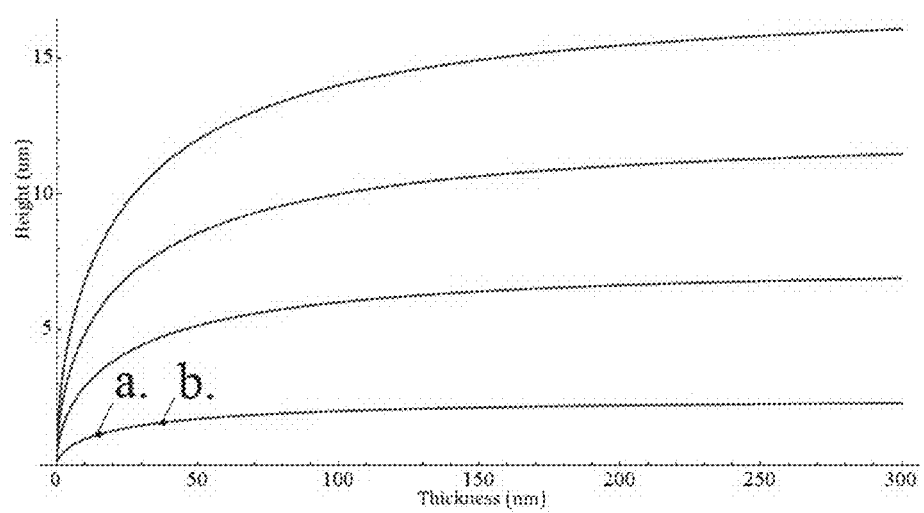

FIGS. 6A-C show computed mode profiles for a coupled resonant plasmonic structure having a depth gradient, illustrating the effect of a gradient thickness on the spatial dependence of mode trapping. In FIG. 6A, the groove thickness is 15 nm, while in FIG. 6B, the gradient is the same as in FIG. 6A, but with the groove thickness is 35 nm. The result of the change in the groove thickness is that the mode in FIG. 6A is trapped in a different location than that of the mode in FIG. 6B. FIG. 6C plots a family of curves showing the first four modes of the coupled plasmonic resonator. Points A and B on the lowermost curve correspond to the structures of FIG. 6A and FIG. 6B respectively, identifying the location of the trapping of the fundamental mode as shown.

Figure 7A:
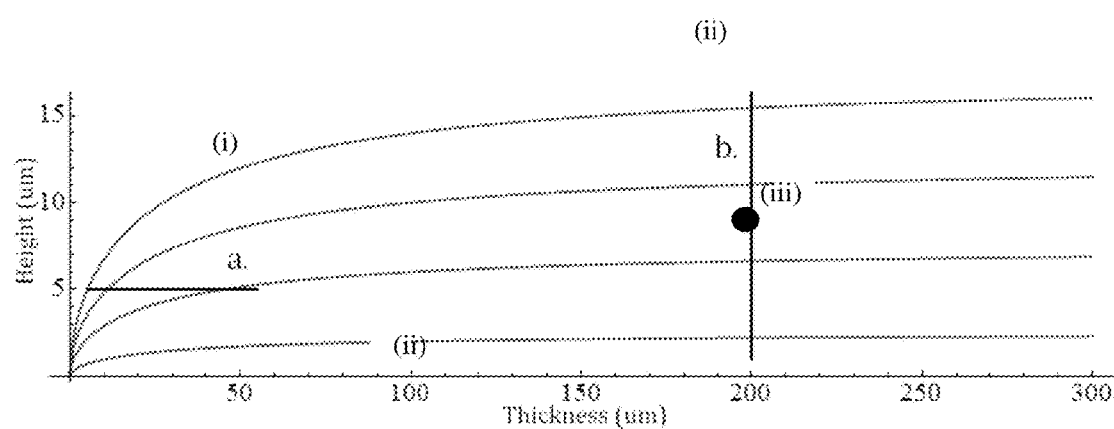
FIG. 7A shows a family of curves plotting the fundamental and higher order modes of a single plasmonic resonator, where lines (i) and (ii) are graphical representations of the structures based on thickness and depth gradients alone, and here point (iii) shows a graded grating outside of the intra-resonator plasmonic coupling regime that trap the fundamental mode.
Figures 7B, 7C:
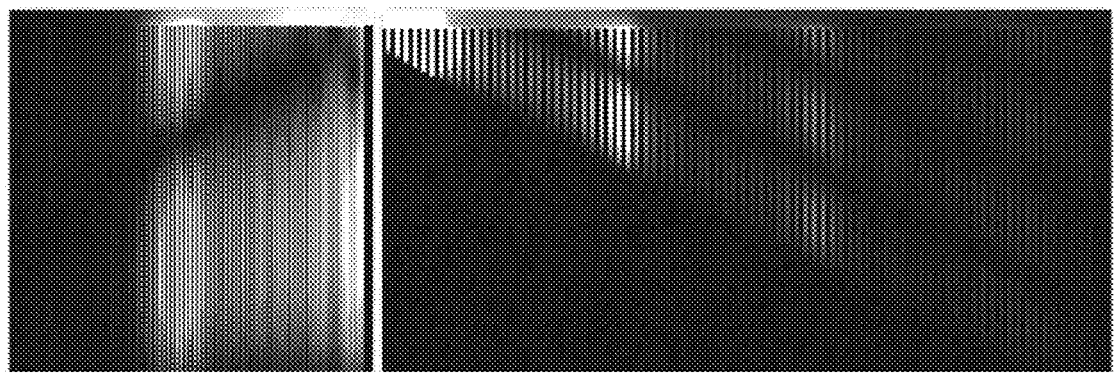
FIGS. 7B and 7C plot mode profiles for (i) a thickness gradient structure corresponding the line (i) in FIG. 7A, and (ii) a depth gradient structure corresponding to the line (ii) in FIG. 7A.

FIG. 7A plots a family of curves corresponding to the fundamental and higher order modes of a single plasmonic resonator, where lines (i) and (ii) are graphical representations of the structures based on thickness and depth gradients alone, and where point (iii) shows a graded grating outside of the intra-resonator plasmonic coupling regime that traps the fundamental mode; and where FIGS. 7B and 7C plot mode profiles for (B) a thickness gradient structure corresponding the line (i) in FIG. 7A, and (C) a depth gradient structure corresponding to the line (ii) in FIG. 7A. In the same manner, any combination of a thickness gradient and a depth gradient, i.e. corresponding to a line in FIG. 7A that makes an angle between 0-90 degrees with the horizontal, may also be described similarly (for example, such as the structure depicted in FIG. 3).

Figure 8:
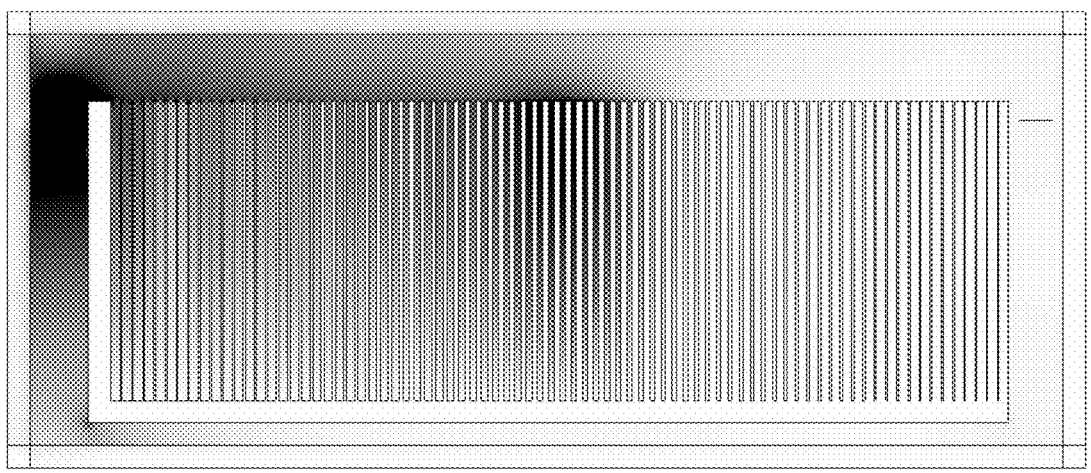
FIG. 8 illustrates the computed mode profile for the structure shown in FIG. 2, illustrating modal trapping.

FIG. 8 illustrates the computed mode profile for the structure shown in FIG. 2, which is based only on a thickness gradient, illustrating modal trapping.

Graded Multiply-Coupled Resonant Plasmonic Structures with Two and Three-Dimensional Gradients Although the preceding example embodiments have described coupled and multiply-coupled resonant plasmonic structures that include planar unit plasmonic resonators having one-dimensional features (i.e. a corrugation extending in one dimension, or holes extending in two dimensions), it is to be understood that the preceding embodiments may be configured to support various two-dimensional or three-dimensional features, propagation and/or confinement, without departing from the intended scope of the present disclosure.

Figure 9:
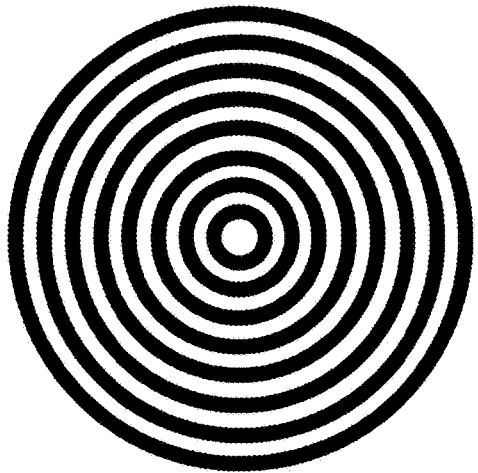
FIG. 9 is a cross-sectional illustration of an example coupled resonant plasmonic structure based on a two-dimensional structure of concentric cylinders.

For example, FIG. 9 is a cross-sectional illustration of a cylindrical coupled resonant plasmonic structure, consisting of a series of concentric conductive cylinders (or non-conductive cylinders with a conductive coating), where the space between each pair of cylinders is occupied by a dielectric to form a unit plasmonic resonator.

Figure 16A:
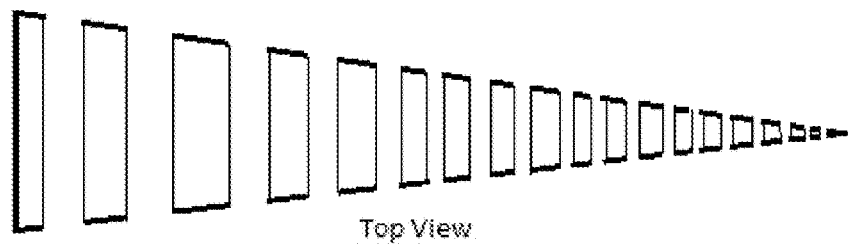
FIGS. 16A-C illustrate views of a structure in which the sideways dimension of the resonator grooves is tapered, which acts as a focusing mechanism of field enhancement towards the direction of wave travel and entrapment.
Figure 16B:
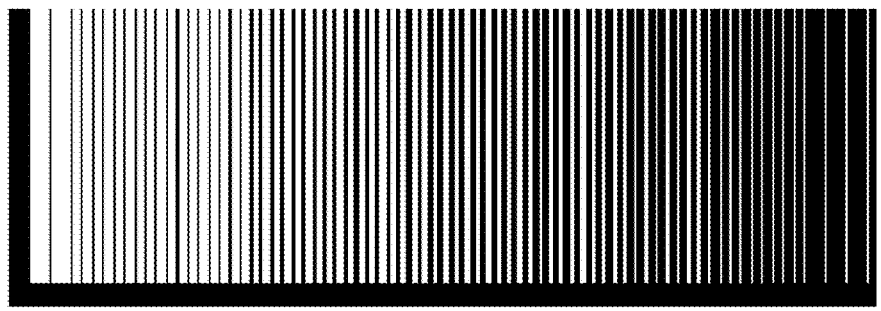
Figure 16C:
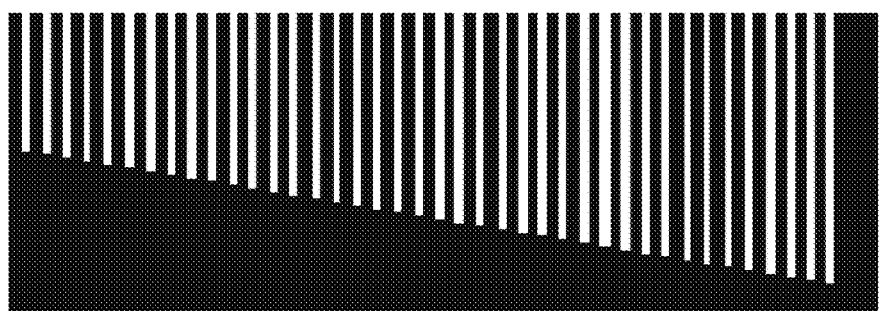

Another geometric example involves the tapering the sideways dimension of the resonator grooves, which will act as a focusing mechanism of field enhancement towards the direction of wave travel and entrapment. An example of such a structure is shown in FIGS. 16A-C.

Figure 13:
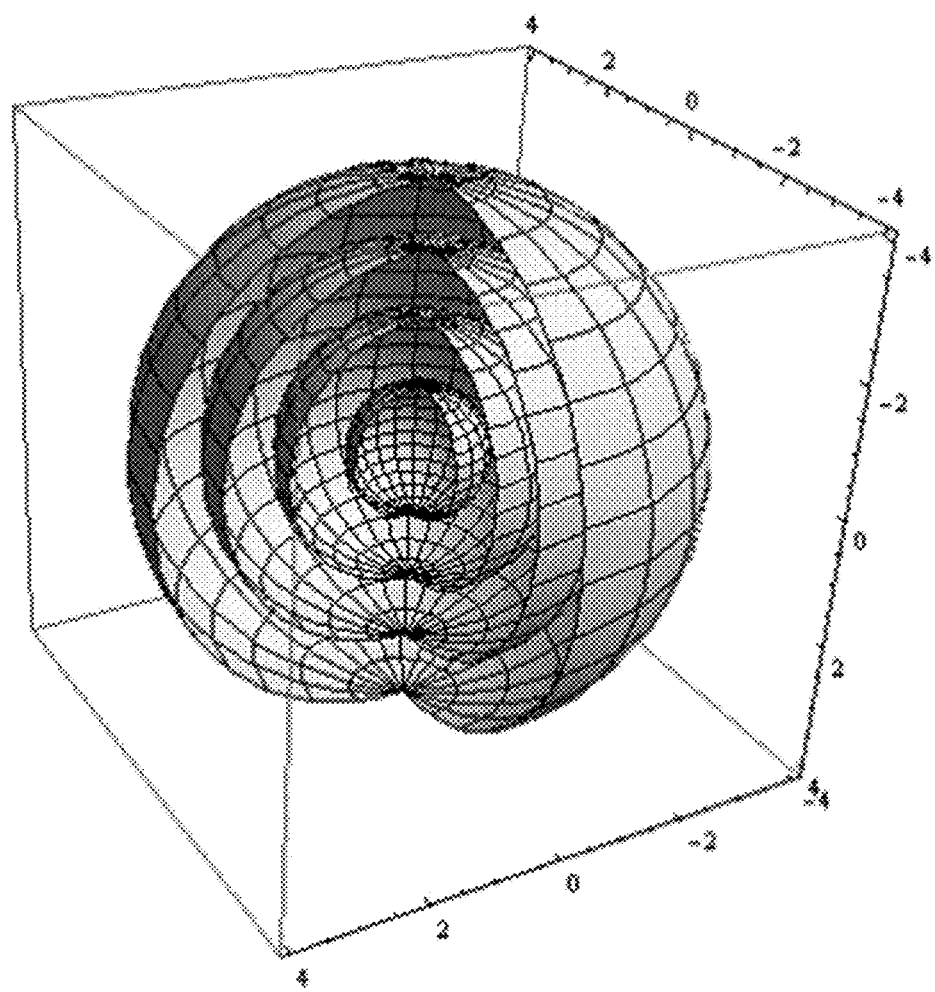
FIG. 13 is an illustration of an example graded coupled resonant plasmonic structure based on concentric shells, showing conductive layers and the spacer areas in between which could be a dielectric material.
Figure 14:
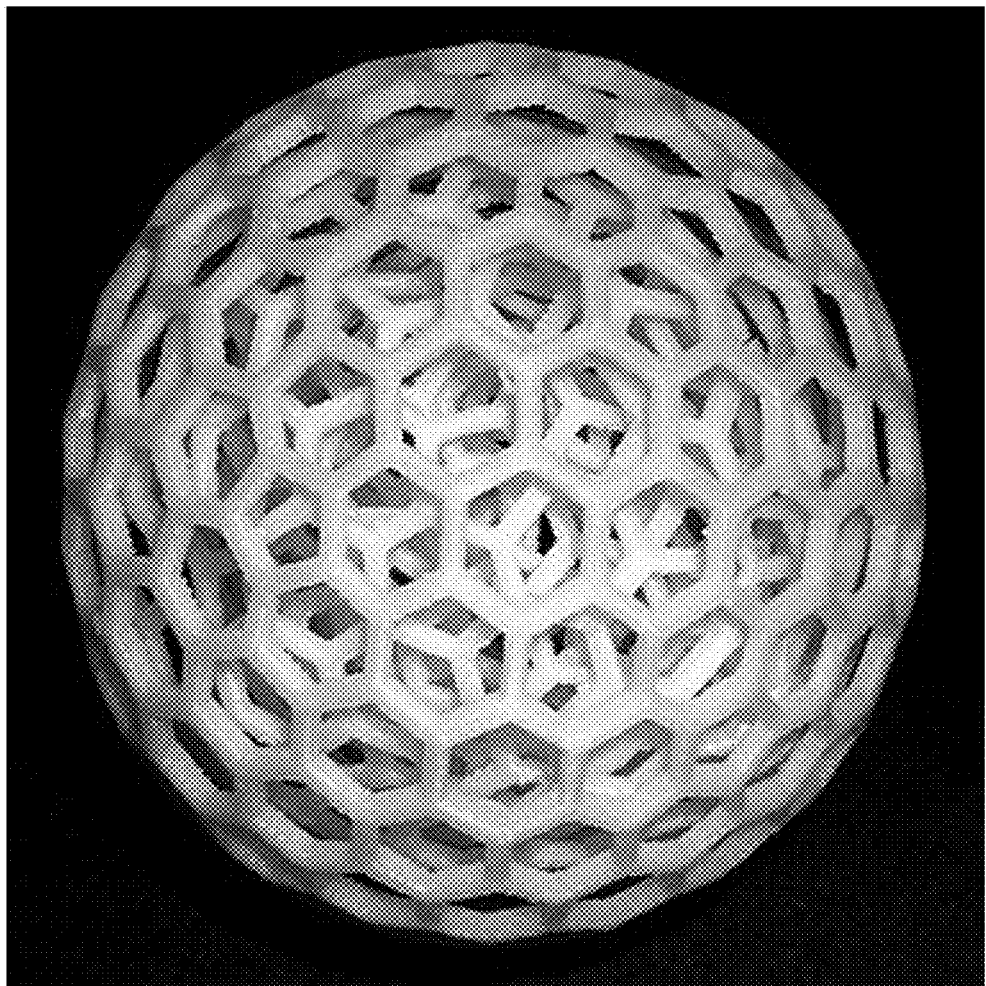
FIG. 14 is an illustration of an example graded coupled resonant plasmonic structure based on a three-dimensional structure of perforated concentric spheres, where the distance between conductive shells is spatially graded.
Figure 15:
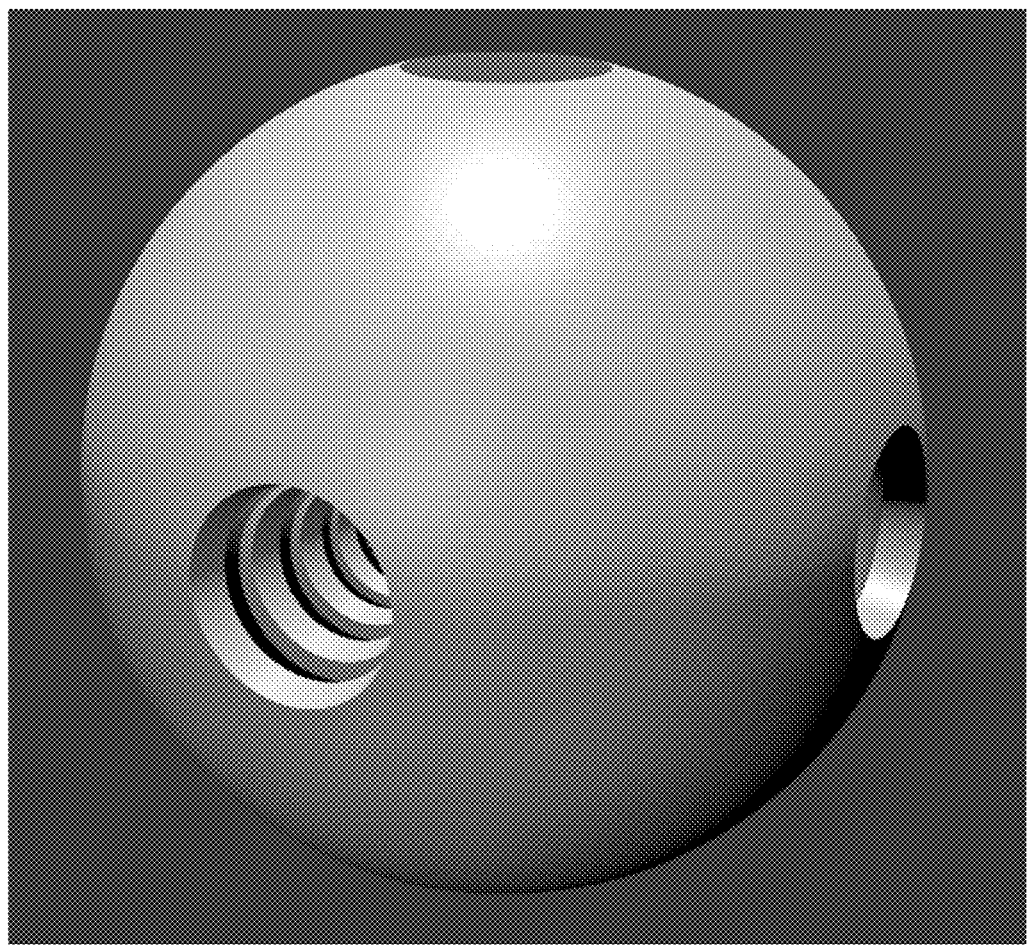
FIG. 15 is an illustration of an example graded coupled resonant plasmonic structure based on a three-dimensional structure of concentric shells, where the generalized geometric gradient utilizes the thickness of the shells, their separation, and/or their surface area.

Similarly, FIGS. 13-15 illustrate embodiments in which a three dimensional set of concentric spherical shells are provided to form a three-dimensional coupled resonant plasmonic structure, where the dielectric gap between spherical shells forms the unit plasmonic resonators, and where holes or other vias in the spherical shells provide apertures to allow the internal propagation of electromagnetic waves.

Such two- and three-dimensional embodiments may be configured such that the distance between adjacent conductive surfaces of the unit plasmonic resonators is sufficiently small to support modal overlap and intra-resonator coupling of surface plasmons, thereby acting as two- and three-dimensional multiply-coupled resonant plasmonic structures.

As in the previously described one-dimensional embodiments, two-dimensional structures can be configured to include a graded structure for controlling, slowing down and/or stopping the group velocity of waves traveling on and within the structure. A generalized geometric grading may be defined as a variation in one or more of the properties (e.g. dimensions) of a coupled plasmonic resonant structure, such that the resonant frequency of the plasmonic resonator changes as a result of such variation.

Figure 10:
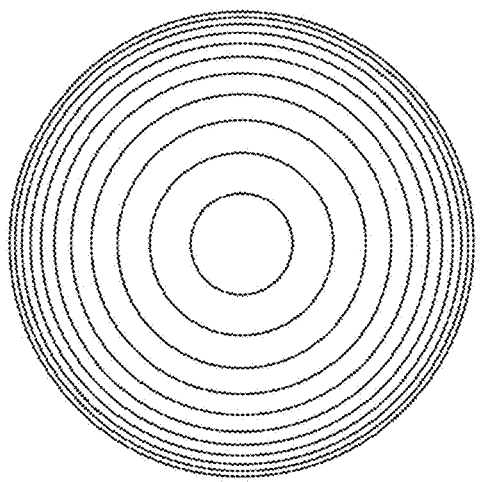
FIG. 10 is a cross-sectional illustration of an example graded coupled resonant plasmonic structure based on a two-dimensional structure of concentric cylinders for which the unit resonator thickness decreases with radius.
Figure 11:
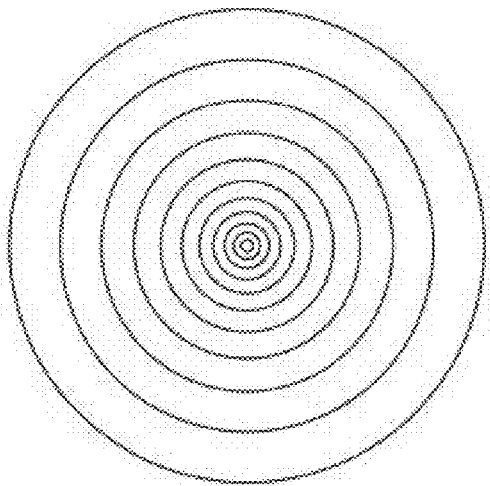
FIG. 11 is a cross-sectional illustration of an example graded coupled resonant plasmonic structure based on a two-dimensional structure of concentric cylinders for which the unit resonator thickness increases with radius.
Figure 12:
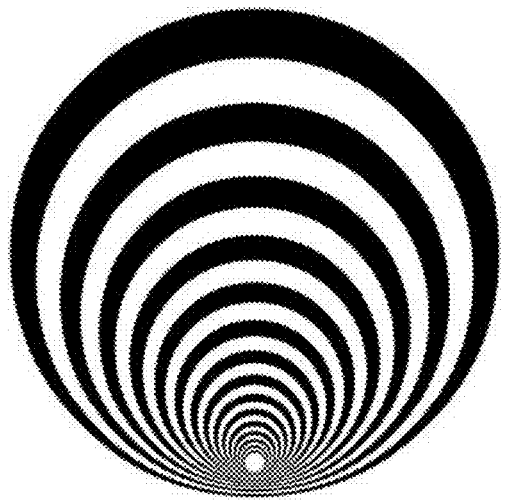
FIG. 12 is a cross-sectional illustration of an example graded coupled resonant plasmonic structure based on a two-dimensional structure of cylinders where the distance between conductive layers (in black), as well as the thickness of the unit resonator gaps, changes as a function of angle as well as the radius.

Examples of graded cylindrical structures are shown in FIGS. 10-12. In FIGS. 10 and 11, the unit plasmonic resonator thickness is graded, with gradient that decreases and increases with radial position in FIGS. 10 and 11, respectively. In FIG. 12, a cylindrical graded coupled resonant plasmonic structure is illustrated in which the unit plasmonic resonators are not concentric, and where a gradient is formed in the unit plasmonic resonator thickness that is dependent on both radius and angle. In other embodiments, a radial, oblique, or eccentric depth gradient may be formed in the cylindrical structure, optionally in additional to another gradient.

The geometric grading of the unit plasmonic resonator dimensions, such as length and thickness, and their effects on the response of the plasmonic structure, may be calculated using the aforementioned methods, and using a diagram such as the one shown in FIG. 5.

It is to be understood that the cylindrical and spherical two- and three-dimensional structures disclosed herein are provided merely as Illustrative examples, and that other two- and three-dimensional shapes and configurations may be employed to form such coupled and multiply-coupled resonant plasmonic structures, with optional gradients in the properties of the unit plasmonic resonators.

The cylindrical devices mentioned above can guide, slow down, or trap radiation along the aforementioned generalized gradient that gradually varies the resonant frequency of adjacent unit plasmonic resonators. For example, in the case of concentric cylinders, where the thickness of the dielectric layer is gradually decreased towards the center, the radial gradient towards the centre would lead to the trapping of radiation at a given radius from the center. This radius can be tuned based on the unit plasmonic resonator parameters previously described, such that a given frequency of radiation is trapped at a specific radius, giving rise to trapped rings or alternatively concentrating the radiation at the center. This trapped/localized/concentrated radiation can be coupled to other structures such as a fiber optic cable, or a nano-antenna.

An alternative structure would use a gradient such that the radiation is directed outwardly from the center. Such a structure would broaden or spread the beam of radiation or light directed at its center. In one embodiment of such a coupled plasmonic structure, the separation between cylinders can be decreased radially outward, so that the light coupled to the center for example by a fiber optic cable is subsequently spread out in a radially outward direction.

Methods of Fabricating Multiply-Coupled Resonant Plasmonic Structures

Depending on the frequency of interest and the device application, several methods may be employed for the fabrication of such multiply-coupled structures. The following section provides several non-limiting examples of such structures.

Existing techniques such as template fabrication, or anisotropic etching of Si described in [A. Polyakov, H. A. Padmore, X. Liang, S. Dhuey, B. Harteneck, J. P. Schuck, and S. Cabrini, "Light trapping in plasmonic nanocavities on metal surfaces," Journal of Vacuum Science & Technology B: Microelectronics and Nanometer Structures, vol. 29, no. 6, p. 06FF01, 2011.] can be used for creating gratings such structures with a thickness gradient. A template fabrication can also use the proper photoresist for electron beam or other source of illumination in which the photoresist itself is used as a template such as described by Polyakov et al.

In this example method, a (110) silicon wafer with a 50 nm of thermally grown silicon dioxide is used. PMMA is used for electron beam lithography with a reliable resolution of 15 nm features. After metallization, lift-off and reactive ion etching (RIE), the resist pattern is converted into an inverse pattern in silicon dioxide which serves as a mask for potassium hydroxide (KOH) anisotropic etch of silicon, that can yield atomically smooth silicon templates for making conductive grating structures. This technique can be used also for concentric cylinder structures.

Another method for fabricating such gratings including concentric cylinders is using photolithography and deep etching into silicon, for example, as described in the David et al. (C. David, J. Bruder, T. Rohbeck, C. Grünzweig, C. Kottler, A. Diaz, O. Bunk, and F. Pfeiffer, Fabrication of diffraction gratings for hard X-ray phase contrast imaging, Microelectronics Engineering 84 (2007), 1172-1177. DOI: 10.1016/j.mee.2007.01.151), Rutishauser et al. (S. Rutishauser, M. Bednarzik, I. Zanette, T. Weitkamp, M. Börner, J. Mohr, and C. David, Fabrication of two-dimensional hard X-ray diffraction gratings, Microelectronics Engineering 101 (2013), 12-16. DOI: 10.1016/j.mee.2012.08.025 PDF), and Rutishauser et al. (S. Rutishauser, I. Zanette, T. Donath, A. Sahlholm, J. Linnros, and C. David, Structured scintillator for hard x-ray grating interferometry, Applied Physics Letters 98 (2011), 171107. DOI: 10.1063/1.3583464 PDF).

Other example methods for fabricating cylindrical coupled plasmonic structure including use a technique such as thermal evaporation, or sputtering, or atomic layer deposition, ALD, or other techniques onto a film and subsequent rolling of that film into a fiber pre-form, and possibly pulling it to obtain thin multilayer fibers similar to a description made in Temelkuran, B., Hart, S. D., Benoit, G., Joannopoulos, J. D. & Fink, Y. Wavelength-scalable hollow optical fibres with large photonic bandgaps for CO2 laser transmission. Nature 420, 650-653 (2002).

Another method for making gratings is layer-by-layer deposition of alternating conductor-dielectric layers using atomic layer deposition, ALD, thermal evaporation, and other processes. Such layered structures can subsequently be cut or otherwise singulated to yield gratings of a desired size and/or shape, including physical manipulation such as bending, pulling, rolling, etc. to yield various desired geometries. By controlling layer thicknesses, for example gradually increasing or decreasing the dielectric thickness, a thickness gradient may be introduced.

For spherical shells, nanoparticle growth techniques can be used, such as using an existing core shell of a fullerene, or other spherical nanoparticle. Subsequently conductive (metallic/plasmonic) such as gold nanoparticles can assemble around the central structure and fused together to form a shell structure. A dielectric is then deposited and the process may be repeated to add layers.

Figure 19:
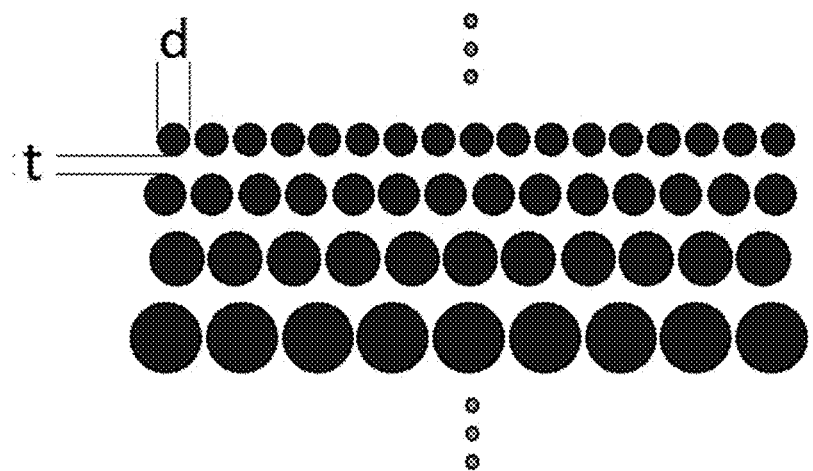
FIG. 19 is an example of a resonant plasmonic structure formed from adjacent layers of nanoparticles, with dielectric therebetween.

Further methods of nanoparticle formation can include chemical growth processes using chemical precursors of metals such as gold and silver, and utilizing gold nano-seed particles on a particular surface including that of a sphere to create a continuous or semi-continuous nanometer thick layer of that metal of the order of a few nanometers to about 100 nm. This method is commonly used for creating metallic nanoparticles, described for instance in: (Huang, X. & El-Sayed, M. A. Gold nanoparticles: Optical properties and implementations in cancer diagnosis and photothermal therapy. Journal of Advanced Research 1, 13-28 (2010)) for various shape nanoparticles and nanoshells. This process can be used to produce a thickness controlled layer. As shown in FIG. 19, the succession of such controlled layer-by-layer deposition can produce a graded plasmonic coupled structure as described in this disclosure. Furthermore, holes or openings can be introduced through the layers to allow electromagnetic waves to propagate within the graded plasmonic coupled structure, or to allow the flow of materials in and out of the structure, while allowing for a possible interaction with the waveguiding and/or light-trapping properties of the graded plasmonic coupled structure.

One rendition of such a structure is shown in FIG. 15. Such openings can be very small, or as large as half a sphere or even larger. Further, the geometry of such grooves can be engineered to provide additional control over the resonant characteristic of the graded plasmonic coupled structure by controlling the surface area of each unit plasmonic resonator, and thus the impedance matching between successive unit plasmonic resonators.

In yet another embodiment, the successive layer-by-layer deposition mentioned above can be done using plasmonic nanoparticles such as gold or silver. Each layer in this embodiment could be varied by changing the layer separation (shown as t in FIG. 19), or the size of the plasmonic nanoparticles involved (shown as d in FIG. 19), or the composition of each nanoparticle.

The plasmonic coupling mentioned in this invention, whereby plasmonic fields of two or more unit plasmonic resonators that are within the plasmonic "earshot" of each other, that is, the surface plasmon fields of one resonator can transfer energy to the other resonator, and whose resonance frequencies are slightly offset, so as to give rise to a resonance gradient, can take many embodiments. Without limiting the scope of the invention the following are some example embodiments:

In one embodiment of this invention, plasmonic nanoparticles, (for example spherical gold or silver nanoparticles though such plasmonic nanoparticles may assume various shapes and be comprised of various plasmonically active materials) are brought within the plasmonic "earshot" of one another, so that the plasmonic fields of at least one particle partially overlap the plasmonic fields of at least another plasmonic nanoparticle that has a slightly different resonance mode. It has been known that coupled waveguides can give rise to a propagation mechanism (Yariv, A., Xu, Y., Lee, R. K. & Scherer, A. Coupled-resonator optical waveguide: a proposal and analysis. Optics Letters 24, 711 (1999)) Similarly, the embodiment mentioned here, uses the strength of inter-particle plasmon coupling as a method to control the propagation of light from one particle to the next. The present invention is different from the existing embodiments in that: 1—The coupling is through plasmonic fields whose resonant frequencies are tunable for example through their size, and/or composition and/or the composition of the dielectric or dielectrics placed between these particles, and 2—there exists a spatial gradient such that at least two such particles with overlapping plasmonic fields have different resonances. The latter can for example be done by smoothly changing the separation of plasmonic particles and/or the size of particles. The result is, that in at least one spatial direction, the effective mode index of the resulting structure and consequently the group velocity of the propagating electromagnetic fields interacting with the plasmonic unit resonators, is modified so as to grant control over the direction and the velocity of electromagnetic wave propagation. It further enables slow light, and light trapping at the region of the layered structure where the plasmonic unit resonators are at resonance with the frequency of the impinging light. As an example, and without intending to limit the range of structures that can emerge with the abovementioned properties, in a layered structure where each layer is comprised of uniform nanoparticles, light-trapping takes place at the location of the layer which is comprised of nanoparticles that are at resonance with the impinging radiation. Such embodiment can be used for coating surfaces, to provide selective absorption, reflection, and transmission of the parts of the spectrum according to whether the structure operates below cutoff, within the resonance band or bands of the structure, or above cutoff. The mentioned devices can be fabricated for example by spin coating of the plasmonic nanoparticle layers, or in some embodiments by sputtering the nanoparticle layers. Subsequently, a dielectric layer is deposited using a deposition techniques such as sputtering, and the process repeats. Accordingly, the size of the nanoparticle layers and their separation are controlled to produce the desired gradient as described here Active and Nonlinear Structures In some embodiments, the structures disclosed herein may be fabricated on, or mechanically coupled to, a mechanically active structure (such as a piezoelectric material or transducer or equivalent) in order to allow the dimensional properties of the structures (and their resulting optical properties, such as mode trapping locations) to be dynamically modified. In another example embodiment, the dielectric region of a unit plasmonic resonator may be formed from an optically nonlinear material, in order to produce plasmonic structures that exhibit optical nonlinear effects such as optical switching, limiting, and bistability near the region of field enhancement.

Solar Devices and Applications

In one example implementation, coupled resonant plasmonic structures may be employed as subwavelength scatterers to facilitate coupling of incident light into guided modes of photovoltaic semiconductor layers, such as Si and GaAs in order to increase carrier generation and/or collection. The photovoltaic layers may be deposited in such a manner so as to optimize each layer to be of a specific composition or bandgap most suitable for a spatial region of the graded plasmonic coupled structure in order to extract maximum light, and thus photocurrent, from each region. That is, photovoltaic materials are deposited in a manner to create a bandgap gradient which most optimally overlaps with the corresponding loci of light trapping in the graded plasmonic coupled structure.

For example, a Si photovoltaic layer may be formed over a region of a multiply coupled resonant plasmonic structure where spatial localization on the structures described here corresponds to the visible range, and a lower bandgap photovoltaic semiconductor structure (such as GaAs) may be formed over the region where IR frequencies are localized. Furthermore, a gradient in the bandgap can be introduced through, for instance, a doping profile to match the loci of light trapping. This can potentially boost efficiency as the bandgaps are fine-tuned to the localized frequencies which are spatially resolved over the plasmonic structures.

In another embodiment, a semiconductor junction can be moved to a desired depth by sandwiching the semiconductor material in a tapered multiply coupled resonant photovoltaic structure, as described above. According to this example embodiment, different wavelengths of light can be concentrated in planes parallel to the surface at a given depth from the surface, in which tapered gratings structures are positioned perpendicular to the surface (as opposed the approach described below in the "Optical Coatings" section in which the tapered gratings are parallel to the surface).

Biosensors

Due to the spatial resolution that the present structures provide, in which different frequencies are trapped at different locations over the structure, which also operates in the THz range, the molecular signatures of most materials can be resolved using the structures disclosed herein.

In some embodiments, molecular sensors may be incorporated above, within, and/or below a multiply-coupled resonant plasmonic structure at various locations, for example by functionalizing the interior of the unit plasmonic resonators by suitable materials (optionally including ligands or other receptor molecules configured to bind to an analyte of interest), or placement of nanodetectors such as nanoantennas within the unit plasmonic resonators. This may enable detection of the presence of certain molecules, if such molecules are present on the path of a wave propagating over the structure prior to it being resolved by the grating, the absorption of frequencies corresponding to their resonances will weaken or remove the signal at the positions of the spatially positioned detectors, indicating the presence of these molecules. Downstream from the path of interaction of light with the specimen, several sensors/detectors can be placed within a single groove to improve accuracy and enhance rejection. Alternatively, several perforations can be turned into sensors in a similar manner.

Another example is the placement of sensors in the centre of the previously described concentric cylindrical structure, and turning the dielectric separator space at a location, for example at radius R, into a microfluidic channel where molecules to be detected are thus introduced. One or more detectors may be at other radial locations (e.g. at the center), to probe the field for the presence and strength of molecular signatures.

Communications

There is a known shortage of suitable materials for transmission of THz radiation. In some embodiments, the structures disclosed herein may be employed as THz transmission media. The structures shown herein, along with the mnemonic key such as the one in FIG. 7A that identify the waveguiding as well as trapping operating regimes, can be employed to design structures that guide, as well as possibly slow down, radiation in the THz regime. Accordingly, coupled or multiply-coupled resonant plasmonic structures may be employed to transfer signals and/or data to different parts of silicon chips and optoelectronics structures. In some embodiments, such structures may be integrated on-chip using existing semiconductor fabrication methods, or modifications thereof.

Optical/Spectral Coatings

In some embodiments, the structures introduced herein be employed as the spectral filters, based on their capability for the trapping and localization of a portion of the radiation spectrum. Furthermore, the unidirectionality of radiation propagation over some of these structures provides additional means of managing electromagnetic wave propagation.

As noted above, multiply-coupled resonant plasmonic structures can be formed by depositing successive layers of metal and dielectric in such a way that the cross-section of the resulting structure be a tapered thickness grating. It is to be understood that such a structure can be made through opening holes, slits, corrugations, and any other partial or full openings in this layered structure, such that the sidewalls of the opening are a tapered grating in the manner described previously. Such opening can be made by laser light, etching, or any other means. Transmission of electromagnetic radiation through such perforation or striation will be influenced by the unidirectional behavior of such tapered gratings and the design of such gratings in accordance with the guidelines given previously. This can for instance be used for light concentration at a particular depth of the structure and selectively transmitting and reflecting radiation based on the design of the gratings that are perpendicular to the plane of the layers.

In one embodiment, after making graded layers through layer by layer deposition, polygonal (e.g. rectangular) or circular holes may be opened through the structure, and these holes may be partially metalized. In the case of a rectangular cross-sectional via, at least one side may be metalized all the way through to create a metallic substrate. Accordingly, each via acts as a grating with unidirectionality and light trapping properties. This embodiment has applications in selectively transmissive coatings, and solar cells. Such structures may be fabricated, for example, by lasers such as femtosecond lasers and subsequently metallizing or by etching.

Smart Fabrics

Structures that trap and localize radiation can act as small sources of heat. This heat can be stored, transferred or reradiated. Trapping of radiation and storing it in a layer can be incorporated in the structure of smart fabrics that trap store heat. This can be achieved, for example, by bringing the localization zone of the structures described herein in close proximity or in contact with a material with a high heat capacity, or a material thermally isolated from outside. This layer can for instance be incorporated inside insulators of clothing to preserve the heat, and perhaps heat up the fabric, in an effect similar to the greenhouse effect. In another embodiment, the unidirectionality of the structures proposed here may be employed such that radiation (including, for example, infrared radiation) is directed towards one side of the fabric. This can be achieved, for example, by arranging tapered plasmonic structures such that the direction of propagation of modes is towards the side where higher temperatures are desired. Since the radiation does not travel back due to the unidirectionality of such structures, an effect similar to the greenhouse effect will result thus keeping the inside of the clothing warmer relative to the outside.

3D Structures for Pharmaceutical Applications

As the three-dimensional structures disclosed herein are scalable and can be configured for light of different frequencies, molecules that are sensitive to a specific frequency may be positioned near the light trapping region of a given structure. For example photochromatic molecules, heat sensitive polymers, and/or other photosensitive or heat-sensitive molecules may be positioned within a multiply-coupled resonant plasmonic structure at a location corresponding to the trapping of a mode of a given frequency. The inclusion of such photosensitive or heat-sensitive molecules may be employed to provide internal barriers that are degraded via directing external radiation of a suitable frequency and a sufficient intensity (or via immersion in a suitable thermal environment). In some embodiments, such internal barriers may be employed to control the release of drugs incorporated into a given structure. Such structures may be introduced into the body and optically activated via external radiation, such as tissue-penetrating infrared radiation.

Security Applications

In some example implementations, resonant plasmonic devices as described herein may be employed to encode information in a secure manner. For example, identification information may be encoded in one or more properties of one or more of the unit plasmonic resonators. In one example embodiment, information may be encoded into variations in the gradient in one or more properties of the unit plasmonic resonators, such that electromagnetic radiation is localized in a unique pattern or spatial distribution. Such a secure identification device may be applied to a wide range of articles, including articles of currency, electronic devices, and other objects.

The following examples are presented to enable those skilled in the art to understand and to practice embodiments of the present disclosure. They should not be considered as a limitation on the scope of the disclosure, but merely as being illustrative and representative thereof.

Examples

Figure 20:
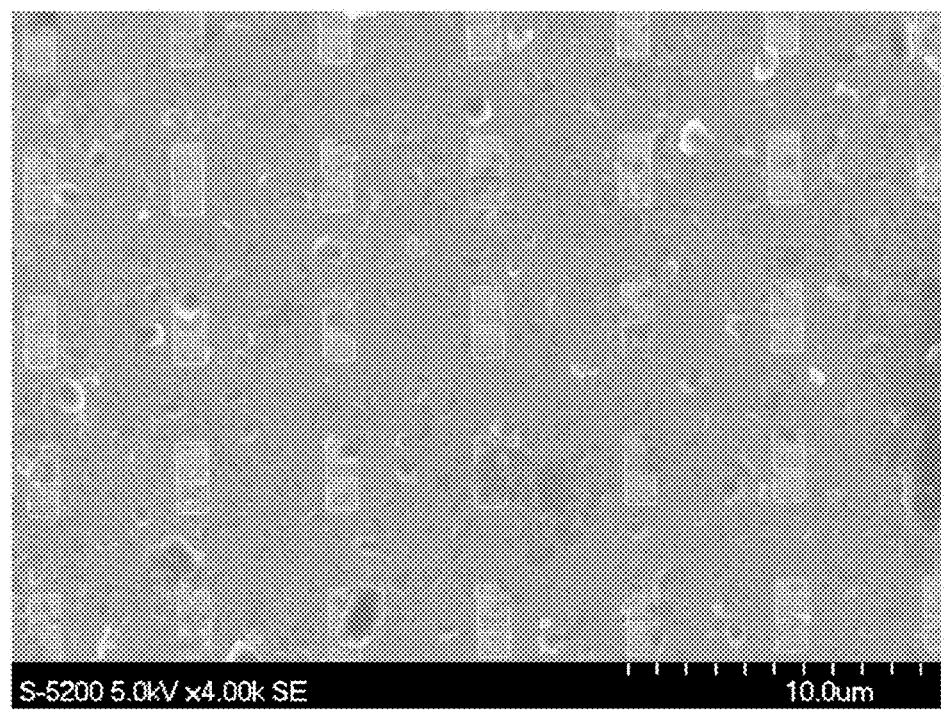
FIGS. 20 and 21 illustrate example resonant plasmonic devices formed using electron beam lithography.
Figure 21:
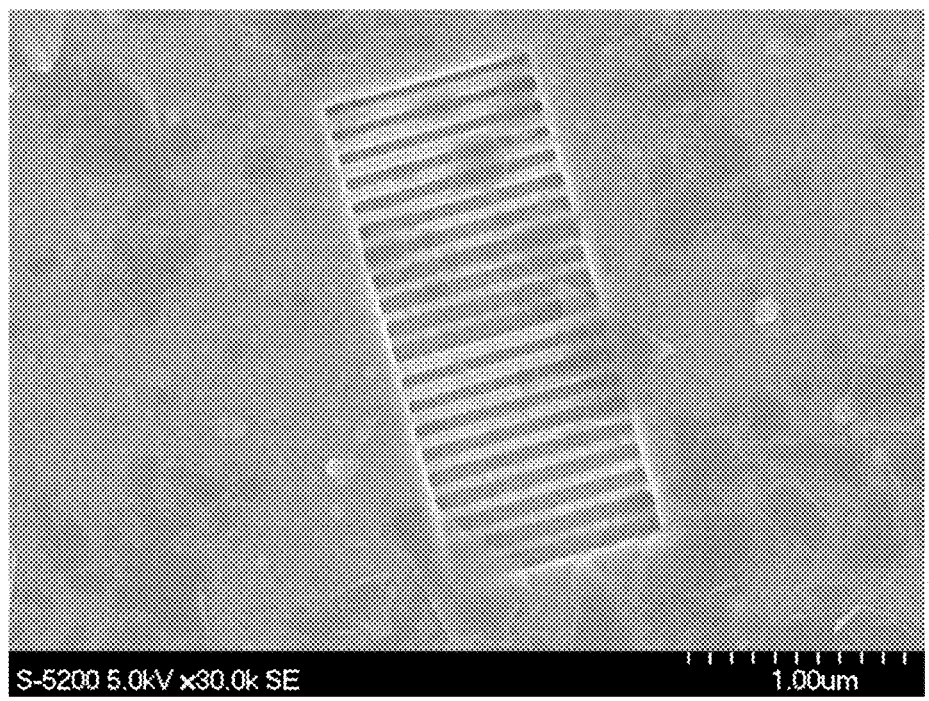

In one example devices fabricated and shown here in FIG. 20 and FIG. 21 using photoresist templating and electron beam lithography. 1—a photoresist such HSQ is deposited on the surface of a sacrificial substrate such as Si, 2—the photoresist is patterned with the negative pattern, 3—a conductor such as silver is deposited using a deposition technique such as sputtering, 4—an adhesive such as epoxy is used to peel off the deposited conductive layer and whatever is left of the photoresist 5—the device is flipped, and optionally the photoresist is removed yielding a surface of coupled plasmonic structure with a variation in the width of the unit plasmonic resonator across the grating. However, any similar technique using for example an anisotropically etched Si or other substrate or other photoresist can be similarly utilized.

Figure 22:
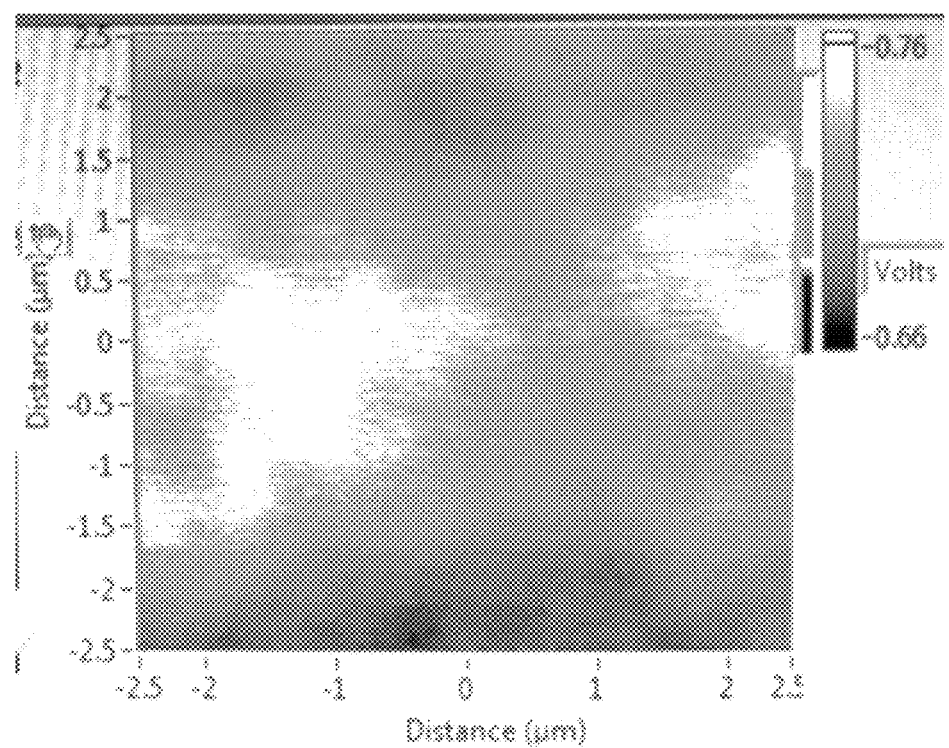
FIG. 22 shows the near-field scanning optical microscopy image of a structure fabricated as previously mentioned, with the lighter regions showing higher intensity fields corresponding to the regions of field concentration.

FIG. 22 shows the near-field scanning optical microscopy image of a structure fabricated as previously mentioned, with the lighter regions showing higher intensity fields corresponding to the regions of field concentration.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives Therefore what is claimed is:

1. A resonant plasmonic device for guiding and localizing electromagnetic radiation, the resonant plasmonic device comprising:
   a support structure comprising a plurality of unit plasmonic resonators;
   each unit plasmonic resonator comprising adjacent conductive surfaces having a dielectric region formed therebetween, thereby defining a resonant cavity;
   wherein a minimum distance between said adjacent conductive surfaces of at least some of said unit plasmonic resonators is configured such that intra-resonator coupling occurs between surface plasmons excited within said adjacent conductive surfaces; and
   wherein neighbouring unit plasmonic resonators are configured to support the coupling of electromagnetic energy therebetween; and
   wherein a spatial gradient in intra-resonator coupling exists among at least a subset of said plurality of unit plasmonic resonators.

2. The resonant plasmonic device according to claim 1 wherein the spatial gradient in intra-resonator coupling is formed by a spatial gradient in the minimum distance between adjacent conductive surfaces.

3. The resonant plasmonic device according to claim 1 wherein each unit plasmonic resonator extends in a longitudinal direction and has a depth associated therewith, and wherein a spatial gradient is provided in said depth in addition to said spatial gradient in intra-resonator coupling.

4. The resonant plasmonic device according to claim 1 wherein the spatial gradient in intra-resonator coupling is formed by a spatial gradient in the effective mode index of said unit plasmonic resonators.

5. The resonant plasmonic device according to claim 1 wherein the spatial gradient in intra-resonator coupling is formed by a spatial gradient in the dielectric constant of said dielectric.

6. The resonant plasmonic device according to claim 1 further comprising a spatial gradient in the distance between adjacent unit plasmonic resonators.

7. The resonant plasmonic device according to claim 1 wherein said adjacent conductive surfaces are partially transparent to the electromagnetic energy, wherein the resonant plasmonic device further comprises a spatial gradient in the thickness of the adjacent conductive surfaces, such that a spatial variation exists in the coupling among adjacent unit plasmonic resonators within said subset of unit plasmonic resonators.

8. The resonant plasmonic device according to claim 1 wherein said unit plasmonic resonators extend in one dimension.

9. The resonant plasmonic device according to claim 8 wherein the unit plasmonic resonators are formed from layers of metallic nanoparticles with dielectric layers provided between the layers of metallic nanoparticles.

10. The resonant plasmonic device according to claim 9 wherein a spatial gradient in the size of said nanoparticles is formed among a plurality of nanoparticle layers.

11. The resonant plasmonic device according to claim 9 wherein a spatial gradient in the thickness of said dielectric layers is formed among a plurality of said dielectric layers.

12. The resonant plasmonic device according to claim 1 wherein said unit plasmonic resonators extend in two dimensions.

13. The resonant plasmonic device according to claim 12 wherein said unit plasmonic resonators are cylindrical shells.

14. The resonant plasmonic device according to claim 13 wherein said unit plasmonic resonators are coaxial.

15. The resonant plasmonic device according to claim 1 wherein said unit plasmonic resonators extend in three dimensions.

16. The resonant plasmonic device according to claim 15 wherein said unit plasmonic resonators are spherical shells having apertures formed therein.

17. The resonant plasmonic device according to claim 1 wherein said unit plasmonic resonators are configured to localize electromagnetic radiation of a pre-selected frequency at a pre-selected location.

18. A solar energy conversion device comprising:
a resonant plasmonic device according to claim 17, wherein said pre-selected location is configured to localize solar radiation associated with a portion of the solar spectrum; and
a photovoltaic device in optical communication with said pre-selected location for collecting optical radiation localized by said resonant plasmonic device.

19. The solar energy device according to claim 18 wherein said unit plasmonic resonators are configured to localize solar radiation associated with different portions of the solar spectrum at different pre-selected locations;
wherein each pre-selected location is in optical communication with a photovoltaic device suitable for converting the localized solar radiation into electrical energy.

20. A controlled release pharmaceutical device comprising:
a resonant plasmonic device according to claim 17; and
a photosensitive substance positioned to be in optical communication with optical radiation localized at said pre-selected location for the controlled release of a medicament.

21. A controlled release pharmaceutical device comprising:
a resonant plasmonic device according to claim 17; and
a thermally absorptive substance positioned to be in thermal communication with thermal radiation localized at said pre-selected location for the controlled release of a medicament.

22. A biosensor comprising:
a resonant plasmonic device according to claim 17; and
wherein said resonant plasmonic device is locally functionalized one or more recognition elements at a location in optical communication with said pre-selected location;
wherein said recognition elements are configured to modulate the transmission of electromagnetic energy through said resonant plasmonic device when an analyte is detected.

23. A security identification article comprising a resonant plasmonic device according to claim 1, wherein identification information is encoded in one or more properties of one or more of the unit plasmonic resonators.

24. A resonant plasmonic device for guiding and localizing electromagnetic radiation, the resonant plasmonic device comprising:
a support structure comprising a plurality of unit plasmonic resonators;
each unit plasmonic resonator comprising adjacent conductive surfaces having a dielectric region formed therebetween, thereby defining a resonant cavity;
wherein neighbouring unit plasmonic resonators are configured to support the coupling of electromagnetic energy therebetween; and
wherein a spatial gradient in the effective mode index of the unit plasmonic resonators exists among at least a subset of said plurality of unit plasmonic resonators.

25. The resonant plasmonic device according to claim 24 wherein the spatial gradient in the effective mode index is provided by a gradient in the minimum distance between said adjacent conductive surfaces.

26. A method of localizing electromagnetic energy within a resonant plasmonic device, the method comprising:
providing a resonant plasmonic device according to claim 1;
directing propagating electromagnetic radiation onto the resonant plasmonic device such that the propagating electromagnetic radiation couples among adjacent unit plasmonic resonators of said resonant plasmonic device;
wherein the electromagnetic radiation comprises at least one frequency associated with a mode that is localized within one or more unit plasmonic resonators within the resonant plasmonic device;
such that at least a portion of the electromagnetic radiation has a reduced group velocity and is localized within the one or more unit plasmonic resonators.

27. A resonant plasmonic device for guiding and localizing electromagnetic radiation, the resonant plasmonic device comprising:
a support structure comprising a plurality of unit plasmonic resonators;
each unit plasmonic resonator comprising adjacent conductive surfaces having a dielectric region formed therebetween, thereby defining a resonant cavity;
wherein a minimum distance between said adjacent conductive surfaces of at least some of said unit plasmonic resonators is less than 100 nm, such that intra-resonator coupling occurs between surface plasmons excited within said adjacent conductive surfaces; and
wherein neighbouring unit plasmonic resonators are configured to support the coupling of electromagnetic energy therebetween; and
wherein a spatial gradient in one or more properties of the unit plasmonic resonators exists among at least a subset of said plurality of unit plasmonic resonators.

28. The resonant plasmonic device according to claim 27 wherein the minimum distance between said adjacent conductive surfaces of at least some of said unit plasmonic resonators is less than approximately 50 nm.

29. A resonant plasmonic device for guiding and localizing electromagnetic radiation, the resonant plasmonic device comprising:
a support structure comprising a plurality of unit plasmonic resonators;
each unit plasmonic resonator comprising adjacent conductive surfaces defining an intra-resonator width, the adjacent conductive surfaces having a dielectric region formed therebetween, thereby defining a resonant cavity;

wherein the width of at least some of said unit plasmonic resonators is configured such that intra-resonator coupling occurs between surface plasmons excited within said adjacent conductive surfaces; and wherein neighbouring unit plasmonic resonators are configured to support the coupling of electromagnetic energy therebetween; and wherein a spatial gradient in the width of the unit plasmonic resonators exists among at least a subset of said plurality of unit plasmonic resonators configured to exhibit intra-resonator coupling.

* * * * *